United States Patent
Van Sickle et al.

(10) Patent No.: US 10,688,261 B2
(45) Date of Patent: Jun. 23, 2020

(54) USAGE MONITORING ATTACHMENT FOR MEDICAMENT DISPENSER

(71) Applicant: Reciprocal Labs Corporation, Madison, WI (US)

(72) Inventors: John David Van Sickle, Oregon, WI (US); Greg Tracy, Madison, WI (US); Mark Gehring, Madison, WI (US); Eric Hoffman, Middleton, WI (US); Kevin Houlihan, Fitchburg, WI (US); Chris Hallberg, Wausatosa, WI (US)

(73) Assignee: Reciprocal Labs Corporation, Madison, WI (US)

( * ) Notice: Subject to any disclaimer, the term of this patent is extended or adjusted under 35 U.S.C. 154(b) by 17 days.

(21) Appl. No.: 16/262,854

(22) Filed: Jan. 30, 2019

(65) Prior Publication Data
US 2019/0231993 A1    Aug. 1, 2019

Related U.S. Application Data

(63) Continuation of application No. 14/770,078, filed as application No. PCT/US2014/039014 on May 21, 2014, now Pat. No. 10,220,166.
(Continued)

(51) Int. Cl.
*A61M 15/00* (2006.01)
*G06F 19/00* (2018.01)
*G16H 20/13* (2018.01)

(52) U.S. Cl.
CPC .......... *A61M 15/008* (2014.02); *A61M 15/00* (2013.01); *A61M 15/0021* (2014.02);
(Continued)

(58) Field of Classification Search
CPC ............ A61M 15/008; A61M 15/0021; A61M 15/00; A61M 15/0048; A61M 15/009; A61M 2202/064; A61M 2205/3303; A61M 2205/332; A61M 2205/3375; A61M 2205/3553; A61M 2205/3592; A61M 2205/50; A61M 2205/52;
(Continued)

(56) References Cited

U.S. PATENT DOCUMENTS 5,363,842 A   11/1994  Mishelevich et al.
6,076,521 A    6/2000  Lindahl et al.
(Continued)

OTHER PUBLICATIONS

Patent Cooperation Treaty, International Search Report and Written Opinion of the International Searching Authority, International Patent Application No. PCT/US2014/039014, dated Oct. 23, 2014, 16 Pages.

*Primary Examiner* — Andrew S Lo
(74) *Attorney, Agent, or Firm* — Fenwick & West LLP

(57) ABSTRACT

Systems and methods are described for monitoring usage of a medicament dispenser—particularly an inhaled medicament dispenser. While operating in a low-power mode, a first sensor is monitored for a signal indicative of handling of the medicament dispenser by a user. In response to detecting such handling, the device exits the low-power mode and begins to monitor a second sensor for a signal indicative of dispensing of the medicament. The usage monitoring device can be embodied as an attachment configured to be selectively coupled to one of a variety of different inhalers including, for example, a Diskus-type inhaler and a Respimat-type inhaler.

20 Claims, 17 Drawing Sheets

Related U.S. Application Data

(60) Provisional application No. 61/825,668, filed on May 21, 2013.

(52) U.S. Cl.
CPC .......... *G06F 19/00* (2013.01); *G06F 19/3462* (2013.01); *G16H 20/13* (2018.01); *A61M 15/009* (2013.01); *A61M 15/0048* (2014.02); *A61M 2202/064* (2013.01); *A61M 2205/332* (2013.01); *A61M 2205/3303* (2013.01); *A61M 2205/3375* (2013.01); *A61M 2205/3553* (2013.01); *A61M 2205/3592* (2013.01); *A61M 2205/50* (2013.01); *A61M 2205/52* (2013.01); *A61M 2205/581* (2013.01); *A61M 2205/583* (2013.01); *A61M 2205/8206* (2013.01)

(58) Field of Classification Search
CPC ...... A61M 2205/581; A61M 2205/583; A61M 2205/8206; G06F 19/3462
USPC .................................................. 128/203.12
See application file for complete search history.

(56) References Cited

U.S. PATENT DOCUMENTS

| | | |
|---|---|---|
| 6,190,326 B1 | 2/2001 | McKinnon et al. |
| 6,202,642 B1 | 3/2001 | McKinnon et al. |
| 8,807,131 B1 | 8/2014 | Tunnell et al. |
| 2003/0221687 A1 | 12/2003 | Kaigler |
| 2007/0023034 A1 | 2/2007 | Jongejan et al. |
| 2008/0125724 A1 | 5/2008 | Monroe |
| 2010/0192948 A1 | 8/2010 | Sutherland et al. |
| 2011/0043357 A1 | 2/2011 | Peatfield et al. |
| 2011/0253139 A1 | 10/2011 | Guthrie et al. |
| 2011/0290256 A1 | 12/2011 | Sather et al. |
| 2016/0144141 A1 | 5/2016 | Biswas et al. |
| 2016/0325057 A1 | 11/2016 | Morrison et al. |
| 2017/0224939 A1 | 8/2017 | Anderson et al. |

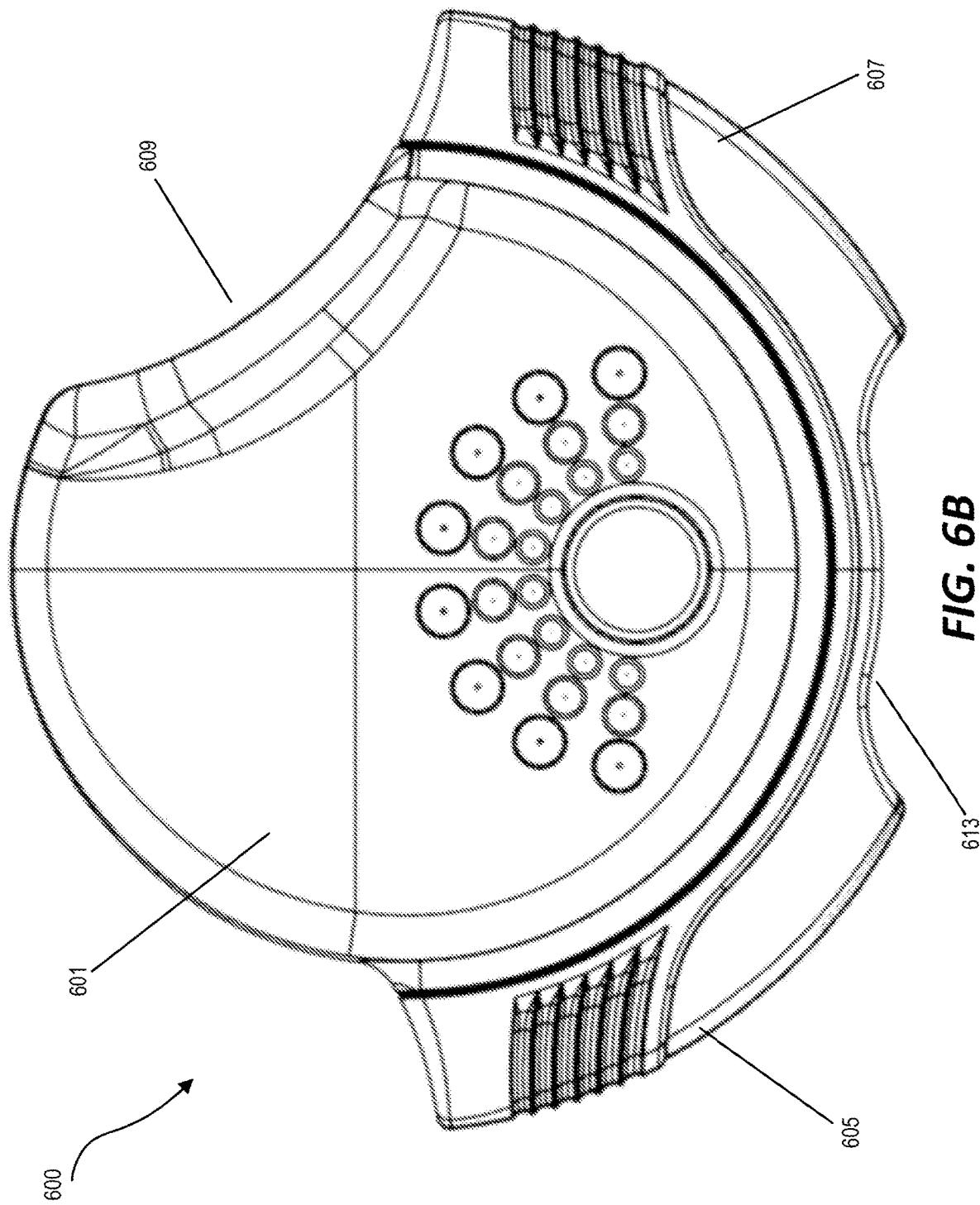

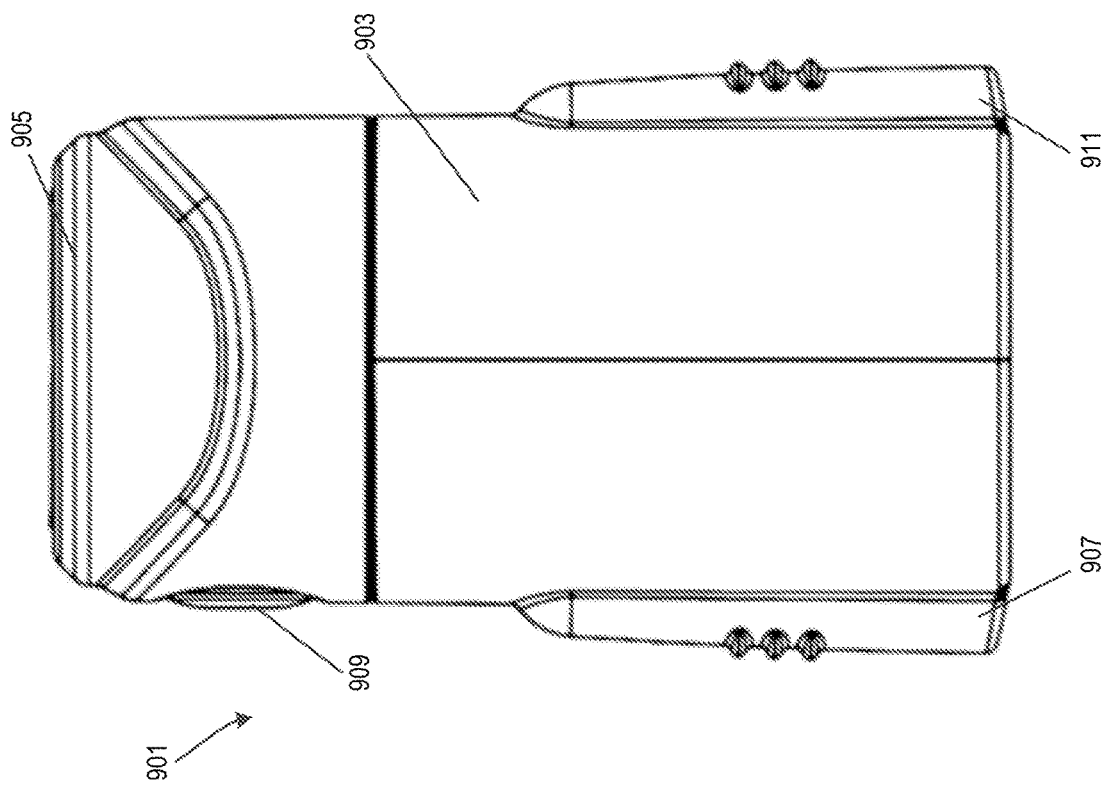
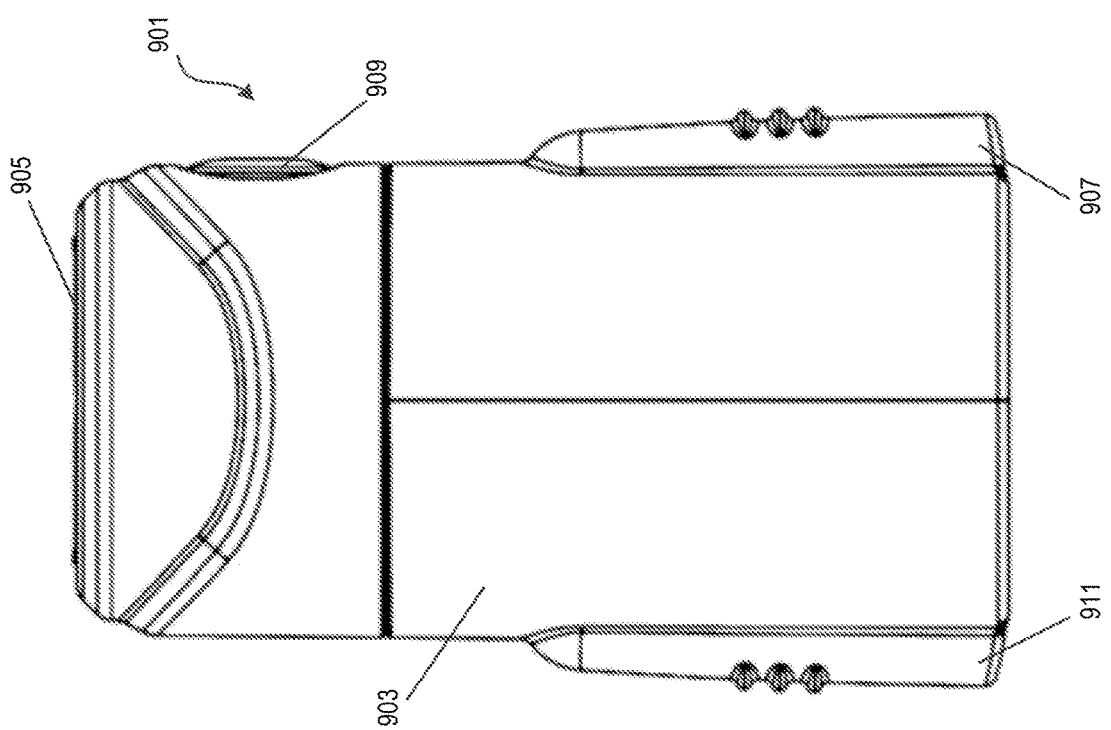
FIG. 8E
FIG. 8D

USAGE MONITORING ATTACHMENT FOR MEDICAMENT DISPENSER

CROSS REFERENCE TO RELATED APPLICATIONS

This application is a continuation of prior, co pending U.S. application Ser. No. 14/770,078, filed on Aug. 24, 2015, which is a National Stage Entry of International Application No. PCT/US2014/039014, filed on May 21, 2014 which claims the benefit of and priority to U.S. Provisional Application No. 61/825,668, filed on May 21, 2013, all of which are incorporated herein by reference in their entirety for all purposes.

BACKGROUND

This The present invention relates to systems and methods for monitoring the usage of a medication. In particular, the invention relates to methods of monitoring usage of a dispenser, such as an inhaler, that provides a dose of medication to a patient.

SUMMARY

In one embodiment, the invention provides an attachment component that is selectively connectable to a medication dispenser. The attachment component includes a controller in communication with an acceleration sensor, at least one infrared sensor, and a microphone. The controller monitors the acceleration sensors and, when the acceleration exceeds a threshold, the controller provides power to the infrared sensors. The controller then monitors the infrared sensor to determine whether a dispenser cover is opened. When the dispenser cover is opened, the controller monitors the acceleration sensor to detect an acceleration associated with a priming of the dispenser. In some embodiments, the "priming" includes activating a mechanism to release a dose of a medication from a packaging. In other embodiment, the "priming" includes a rapid shaking of a medication canister. After the priming action is detected, the controller activates the microphone and records an audio signal for a defined duration of time. In some embodiments, the controller terminates recording when the infrared sensors indicate that the dispenser cover is closed.

In some embodiments, the controller performs one or more audio processing operations on the recorded audio signal. In some embodiments, the controller transmits the audio recording or data indicative of the audio record through a wireless transceiver device to a portable telephone. In some embodiments, the attachment further includes a wired data port for connecting the attachment to an external device such as a personal computer. When the wired data port is connected to the external device, the controller transmits the audio recording or data indicative of the audio recording through the wired data port.

In one embodiment, the invention provides a method of monitoring usage of a medicament dispenser. While operating in a low-power mode, a first sensor is monitored to detect handling of the medicament dispenser by a user. Once handling of the dispenser is detected, the low-power mode is exited and power is applied to a second sensor. The second sensor is then monitored for a signal indicative of dispensing of the medicament.

In another embodiment, the invention provides a method of monitoring usage of a medicament dispenser. A monitoring attachment is coupled to a medicament dispenser such that the monitoring attachment does not interfere with dispensing of medicament from the medicament dispenser. The monitoring attachment is operated in a low-power mode, wherein power is applied to an acceleration sensor positioned within the monitoring attachment when in the low power mode and power is not applied to a second sensor positioned within the monitoring attachment when in the low-power mode. While operating in the low-power mode, the acceleration sensor is monitored and the output is compared to an acceleration threshold. When the output of the acceleration sensor exceeds the acceleration threshold, the attachment determines that the medicament dispenser (and the attachment) is being handled by a user. In response, the attachment exits the low-power mode and applies power to the second sensor. The second sensor is then monitored for a signal indicative of dispensing of a medicament from the medicament dispenser in response to determining that the monitoring attachment is being handled by the user. In response to detecting the signal indicative of the dispensing of medicament, the attachment transmits a signal through its wireless transmitter indicative of the dispensing of the medicament.

In various embodiments, the attachment is configured to be selectively coupled to different specific inhaler types including, for example, a Diskus-type dry-powder inhaler or a Respimat-type soft mist inhaler.

In yet another embodiment, the invention provides an attachment for monitoring usage of a medicament dispenser. The attachment includes a housing that is selectively coupleable to the medicament dispenser without affecting the operation of the medicament dispenser. A first sensor, a second sensor, and a wireless transmitter are fixedly coupled to the housing. The attachment also includes a processor and memory. The attachment operates in a low-power mode where power is applied to the first sensor and power is not applied to the second sensor. While in the low-power mode, the attachment monitors the first sensor for a signal indicative of handling of the medicament dispenser while operating in the low-power mode. In response to detecting such a signal, the attachment exits the low-power mode, applies power to the second sensor, and monitors the second sensor for a signal indicative of dispensing of the medicament from the dispenser. Once the dispensing is detected, the attachment transmits a signal indicative of the dispensing through its wireless transmitter.

In some embodiments, the housing of the attachment includes an upper body portion and a lower body portion. The upper and lower body portions are connected by one or more side support structures and are sized to receive a Diskus-type medicament dispenser between the upper body portion and the lower body portion such that the upper body portion is positioned on a top surface of the substantially disc-shaped dispenser body and the lower body portion is positioned on a bottom surface of the substantially disc-shaped dispenser body.

Other aspects of the invention will become apparent by consideration of the detailed description and accompanying drawings.

BRIEF DESCRIPTION OF THE DRAWINGS

FIG. 6B is a top view of the attachment of FIG. 6A.

FIG. 8D is a left side view of the attachment of FIG. 8A.

FIG. 8E is a right side view of the attachment of FIG. 8A.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1A:
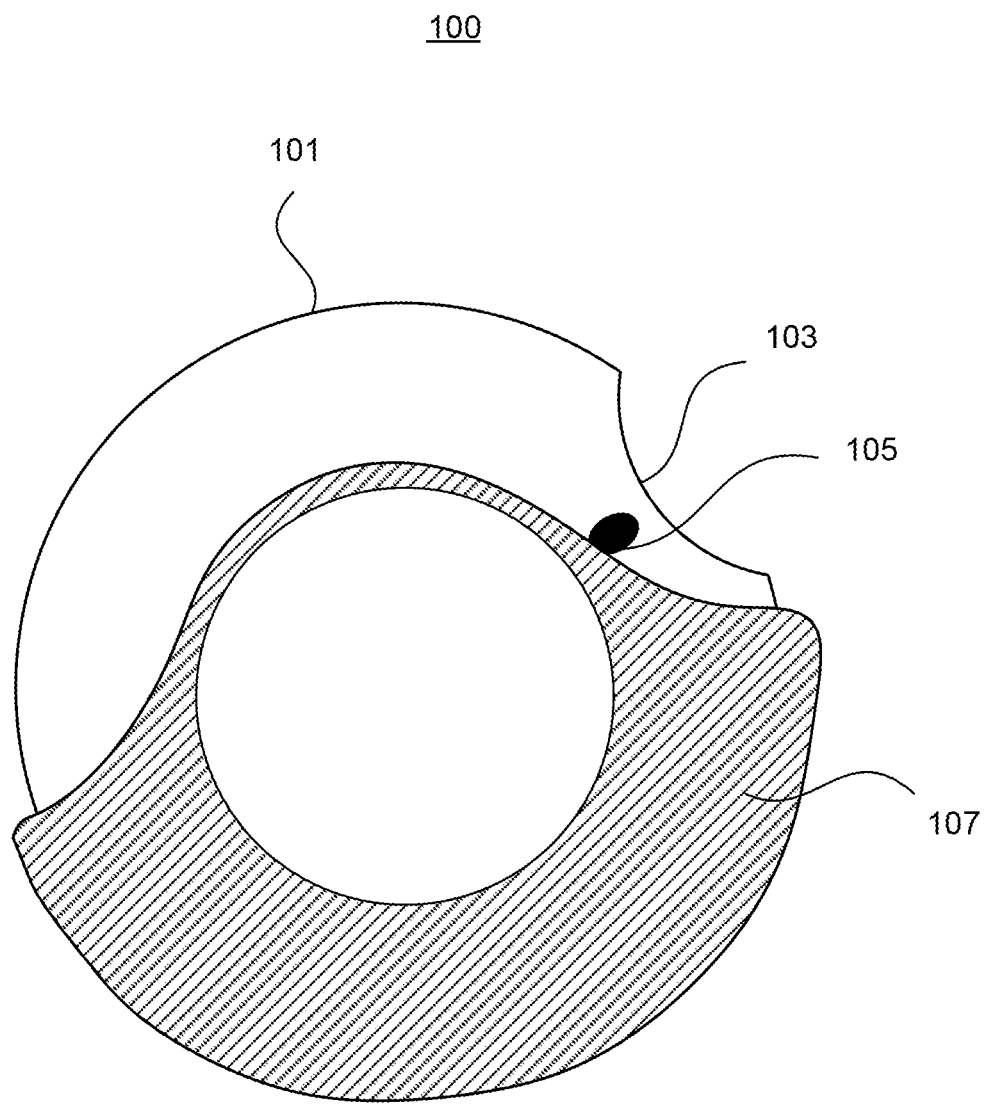
FIG. 1A is an overhead view of a medication dispenser in a closed position.

FIG. 1A illustrates an example of a device 100 for dispensing an inhaled medication such as the Advair Diskus® dry powder inhaler (DPI). The dispenser 100 includes a dispenser body 101, a thumb grip 103, and a dose counter 105. A rotatable cover 107 is rotatably connected to the dispenser body 101. To place the dispenser device 100 in the "open" position, a user places her thumb in the thumb grip 103 and rotates the dispenser body 101 relative to the dispenser cover 107 as indicated by the arrow.

Figure 1B:
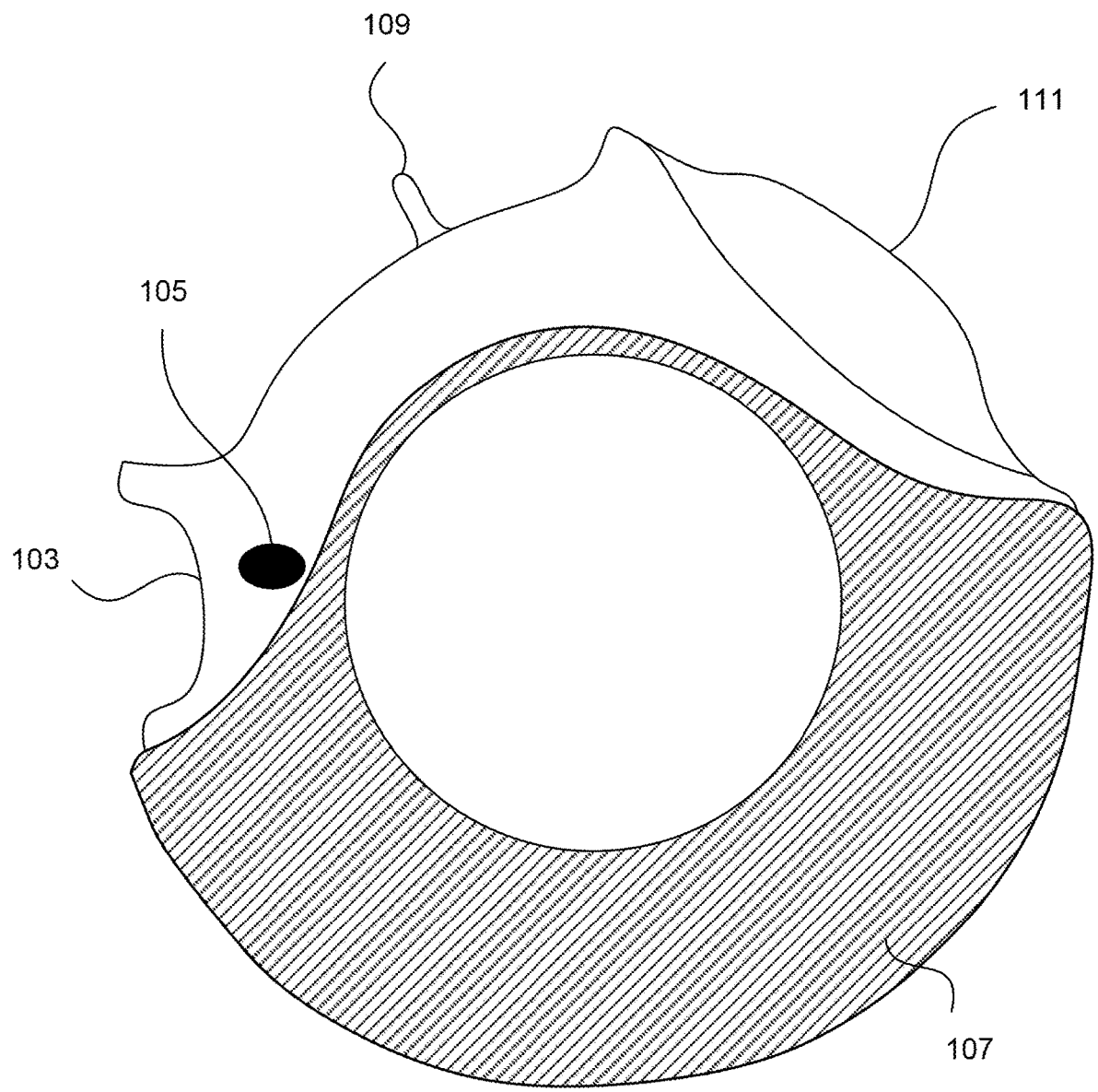
FIG. 1B is an overhead view of the medication dispenser of FIG. 1A in an opened position.

FIG. 1B shows the dispenser device 100 in the open position. Because the dispenser body 101 has been rotated relative to the cover 107, the thumb grip 103 and the dose counter 105 are now shown on the opposite side of the device 100. When in the open position, a priming lever 109 and a mouthpiece 111 of the device 100 are uncovered.

To use the dispenser device shown in FIGS. 1A and 1B, a patient rotates the dispenser body 101 into the "open" position and moves the priming lever 109 as indicated by the arrow in FIG. 1B. Moving the priming lever 109 causes a dose of medication to be removed from packaging stored within the device body 101. In some constructions, moving the priming lever 109 both removes a medication from a packaging and crushes a pill-form medication into an inhalable powder. The patient then places their mouth on the mouthpiece 111 and inhales the medication from the dispenser 100.

Figure 2:
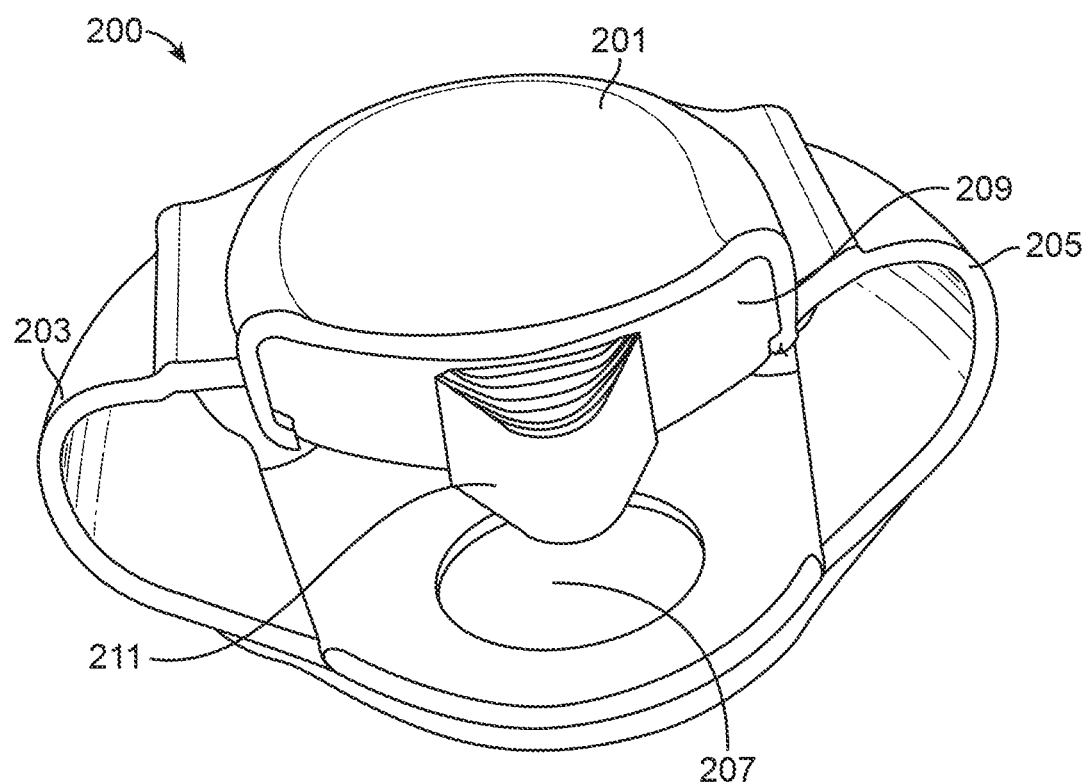
FIG. 2 is a perspective view of an attachment for monitoring usage of the medication dispenser of FIG. 1A according to one embodiment.

FIG. 2 illustrates an attachment device 200 that monitors usage of the dispenser 100. Data collected from the attachment device 200 can be used to track the time, date, and location of regular uses of a medicament dispenser, such as described in U.S. Pub. No. 2009/0194104, filed on Jan. 5, 2009 and entitled "DEVICE AND METHOD TO MONITOR, TRACK, MAP, AND ANALYZE USAGE OF METERED-DOSE INHALERS IN REAL-TIME." Alternatively, the collected data can be analyzed to confirm that the medication is being taken appropriately. For example, the data can be analyzed to verify that the medication is being taken at the appropriate times as prescribed by the doctor. Furthermore, as described in further detail below, the audio signal recorded during usage can be analyzed to ensure that the medication is being properly inhaled and, in some cases, to confirm that the proper medication is being used.

As shown in FIG. 2, the attachment device 200 includes an upper body 201 with two leg portions 203,205 extending from the upper body 201 and reconnecting at a lower ring body 207. A medication dispenser, such as dispenser 100 illustrated in FIGS. 1A & 1B is selectively insertable into the cavity formed by the upper body 201, the leg portions 203,205, and the lower ring body 207. The attachment device 200 is also water proof (or water resistant) to protect the electronics housed within. The attachment device 200 is constructed of a bio-compatible material that will not adversely affect the medication being dispensed and will not adversely affect the patient using the device 200.

The attachment device 200 is sized to receive the dispenser 200 and hold the dispenser in place by friction. In some constructions, all external surfaces of the attachment device 200 are constructed of a rigid plastic material. However, in some alternative constructions, the leg portions 203, 205 are construction of a flexible and stretchable material to allow the attachment device to better conform to the dispenser and to increase friction between the attachment and the dispenser.

The attachment device 200 is sized and shaped so that it does not interfere with the operation and actuation of the medication dispenser or with the dispensed medication. The priming lever 109 is able to move freely and access to the mouthpiece 111 is not obstructed. When there are no more medication doses remaining in the dispenser 100, the dispenser 100 can be removed from the attachment device 200 and replaced with a new dispenser 100. The opening in the lower ring body 207 provides access to the dispenser 100, making it easier for the dispenser 100 to be removed. In some constructions, color coding is used to ensure that the correct dispenser is used and that the dispenser is properly inserted into the attachment device 200.

The attachment device 200 also includes a "cassette" portion 209. The "cassette" portion 209 houses the electronics of the attachment device 200 as described below and can be removed from the upper body 201 of the attachment device 200. The cassette portion 209 includes a protrusion 211 that extends from the upper body 201 when the cassette portion 209 is properly installed. The protrusion 211 positions various sensors—including a pair of infrared sensors that detect whether the dispenser 100 is in the open (FIG. 1B) or closed position (FIG. 1A).

Figure 3:
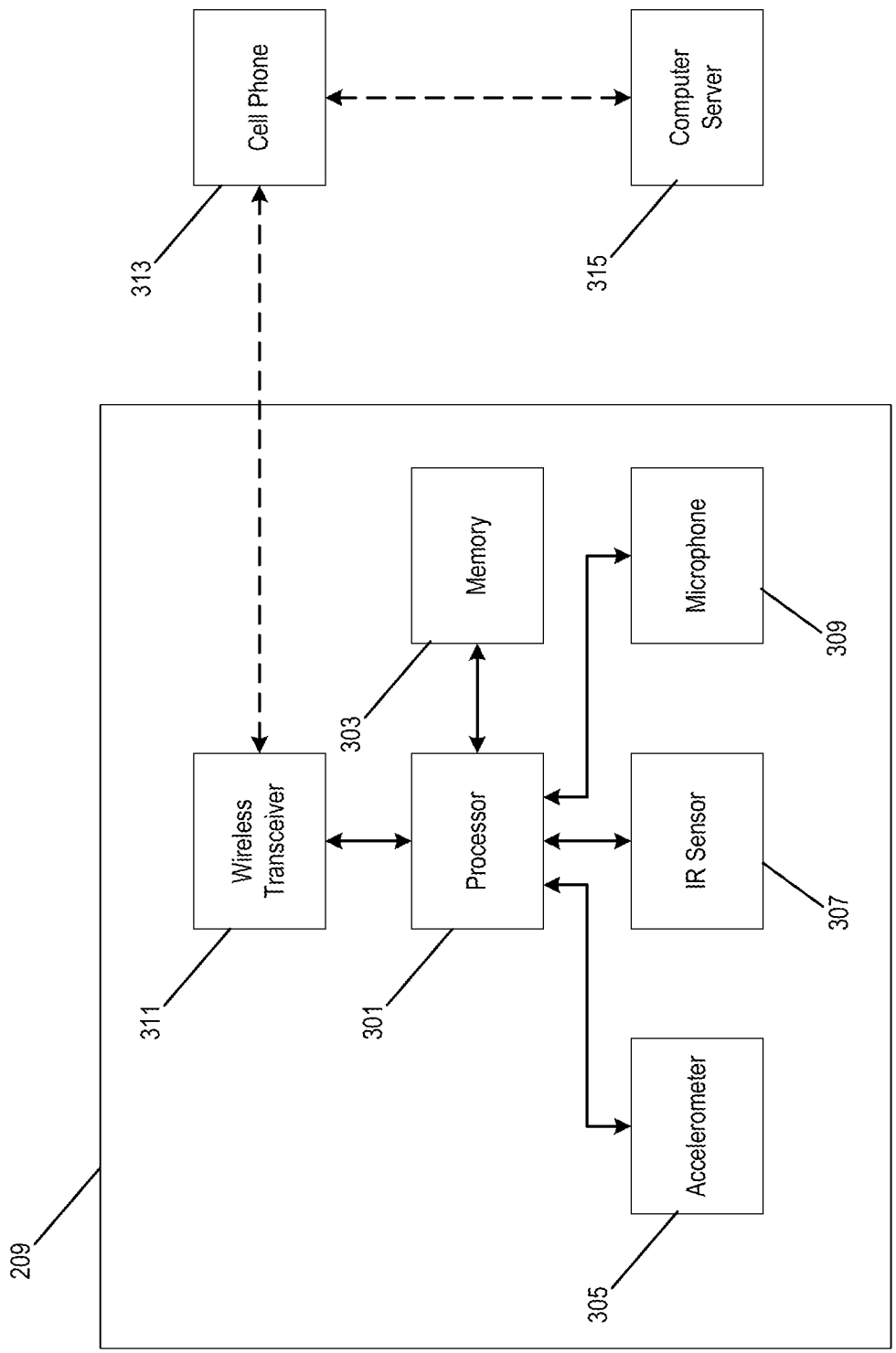
FIG. 3 is a block diagram of various components of the attachment of FIG. 2.

FIG. 3 illustrated the electronic components housed within the cassette portion 209 of the attachment device 200. Although, in this example, the electronics can be removed from the attachment device 200 by removing the cassette portion 209, in other constructions, the electronics can be permanently housed within the upper body 201 or elsewhere in the attachment device 200.

The cassette portion 209 includes a processor 301 which controls the operation of the attachment device 200. In various constructions, the processor 301 can include a microcontroller, microprocessor, ASIC, or other circuitry. However, in this particular example, the processor 301 accesses software instructions stored on a memory 303 and executes the instructions to control the operation of the attachment device 200. The memory 303 can include, for example, one or more transitory or non-transitory memory components such as random access memory ("RAM"), read-only memory ("ROM"), flash memory, and other magnetic memory media. In this example, the memory module 303 includes a non-volatile memory that retains stored data when power is lost (or intentionally removed).

The processor 301 is connected to three sensor modules—an accelerometer 305, an IR sensor module 307, and a microphone 309. The accelerometer 305 measures accelerations applied to the attachment device 200 caused by movements of the device. Furthermore, as described in detail below, the accelerometer 305 may be positioned and configured to detect an impulse caused by the movement of the priming lever 209. The accelerometer 305 includes a low-power, 3-axis accelerometer that is being monitored at all times. Alternatively, the attachment device may include one or more capacitive sensors to detect when the device is being handled.

The IR sensor module 307 includes a pair of infrared sensors positioned in the protrusion 211 of the attachment device 200. The IR sensors are positioned to monitor movements of the device body 201 and to indicate whether the dispenser is in an open position or a closed position. In particular, the IR sensor module monitors the position of the air intake ridges of the dispenser or the location of the dose counter window (depending on how the dispenser is inserted into the attachment device). Although the examples described herein include an IR sensor module, some alternative constructions will include other sensor mechanisms to determine whether a dispenser is opened or closed. For example, a mechanical switch or magnetic detection can be used to detect rotation of the dispenser body.

Alternatively, the attachment housing itself can be constructed of a metalized plastic material or with electrodes which would allow the entire body of the attachment device to operate as a capacitive sensor. Changes in capacitance could be monitored to indicate when the device is being handled—thereby also replacing the accelerometer. In addition, the electrodes can sense when the patient lips are near or contacting the mouthpiece.

The microphone 309 captures audio of the patient inhaling the medication. This audio data is processed by the processor 301 or by an external computer system to ensure appropriate medication usage. Furthermore, the microphone system 309 is configured to identify, note, and segregate inhalation events from other background noise. The microphone system 309 eventually adapts to eliminate false positives by recognizing an audio signal that is associated with a user's unique inhalation. As the microphone system 309 is able to adapt based on "learned" data, the accuracy of the attachment device and its ability to correctly identify inhalation events is improved.

The processor 301 is also connected to a wireless transceiver 311 that is configured to exchange data with an external device. In the example of FIG. 3, the wireless transceiver 311 communicates with a cellular telephone 313 carried by the patient. The cellular telephone 313 further relays information between the attachment device 200 and a remote computer server. The wireless transceiver in this example is a Bluetooth-type transceiver. However, other constructions may include any other type of wireless communication device including, for example, Wi-Fi, cellular, or RF transceivers.

The example of FIG. 3 shows the accelerometer 205, IR sensor module 307, microphone 309, and wireless transceiver 311 all directly connected to the processor 301. However, it is to be understood that the attachment device may include a controller area network ("CAN") with a bus for relaying data between the various components of the attachment device 200. Other configurations and communication mechanisms are also possible.

Furthermore, although the example of FIG. 3 shows communication with the computer server 315 through a wireless relay with a cell phone 313 carried by the user, other constructions may include other mechanisms for transferring data between the attachment device 200 and the computer server 315. For example, the attachment device 200 may be equipped with a cellular communication module for directly communicating with the computer server 315 over a cellular telephone network. Alternatively, the attachment device 200 may include a Wi-Fi transceiver for communicating with the computer server 315 through the Internet or other computer network. Furthermore, wired communication mechanisms can also be utilized. In some constructions, the attachment device includes a wired data port. When the attachment device is directly connected to a personal computer through the wired data port, the controller is configured to communicate with the computer through the wired data port. The wired data port can also be used to provide software/firmware updates to the attachment device.

Figure 4:
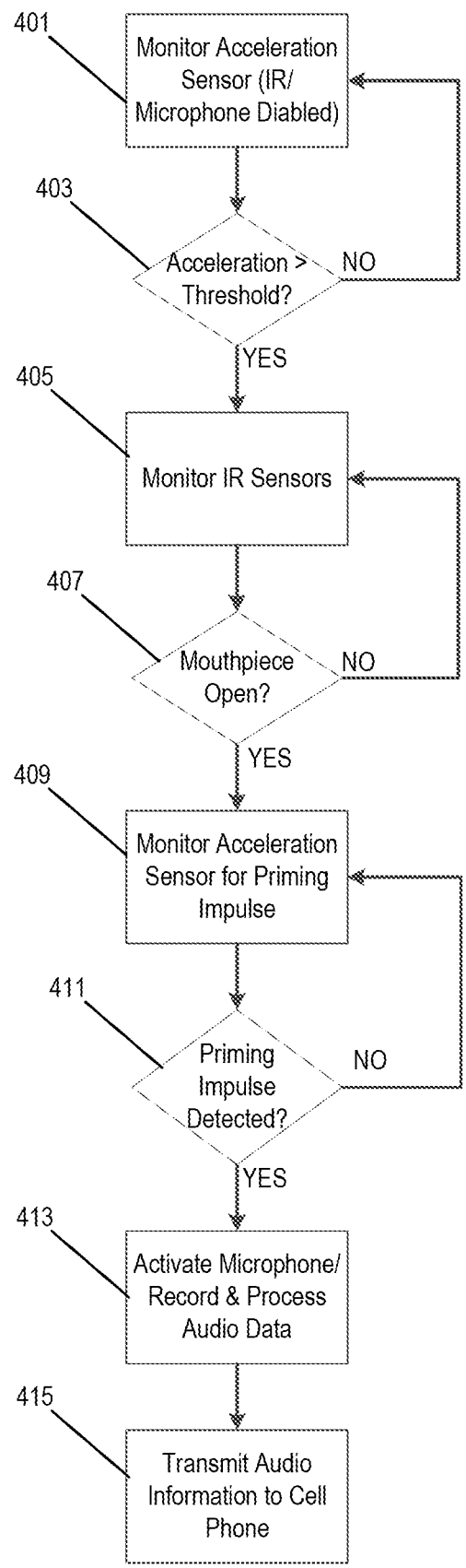
FIG. 4 is a flowchart of a method for monitoring usage of a medication dispenser using the attachment of FIG. 2.

FIG. 4 illustrates one example of a method of monitoring usage of the dispenser 100 using the attachment device 200. The method of FIG. 4 is stored as software instructions on the memory 303 and executed by the processor 301. The attachment device begins in a low-power "sleep mode" where the acceleration sensor is being monitored, but the IR sensor module and the microphone are both disabled (step 401). The controller continuously compares the measured acceleration to an acceleration threshold (step 403). Once the threshold is exceeded-indicating excessive movement of the dispenser device, the controller provides power to the IR sensors (step 405) and monitors the IR sensors to determine whether the dispenser is in an open position or closed position (step 407). Once the IR sensors indicate that the dispenser is in the open position, the controller monitors the acceleration sensor for a motion impulse associated with activation of the priming lever (step 409). When the priming impulse is detected (step 411), the controller activates the microphone and begins recording audio data (step 413). The audio data is amplified, low-pass filtered, and converted to digital data by a 12-bit analog-to-digital converter. The raw digital data is stored to the memory and analyzed (e.g., FFT, cepstral coefficients, zero-crossing rate, average amplitude vs. time, envelope, etc.) to create a compressed set of metadata associated with the recorded audio. The controller then wirelessly transmits the compressed audio data to a cellular phone (step 415) which then sends the data to a computer server for further analysis and determination of whether a detected "usage event" was an actual dispense and inhalation of the medication. Alternatively, in some constructions, the raw, uncompressed audio data is sent to an external system where the audio processing and analysis is later performed.

Figure 5:
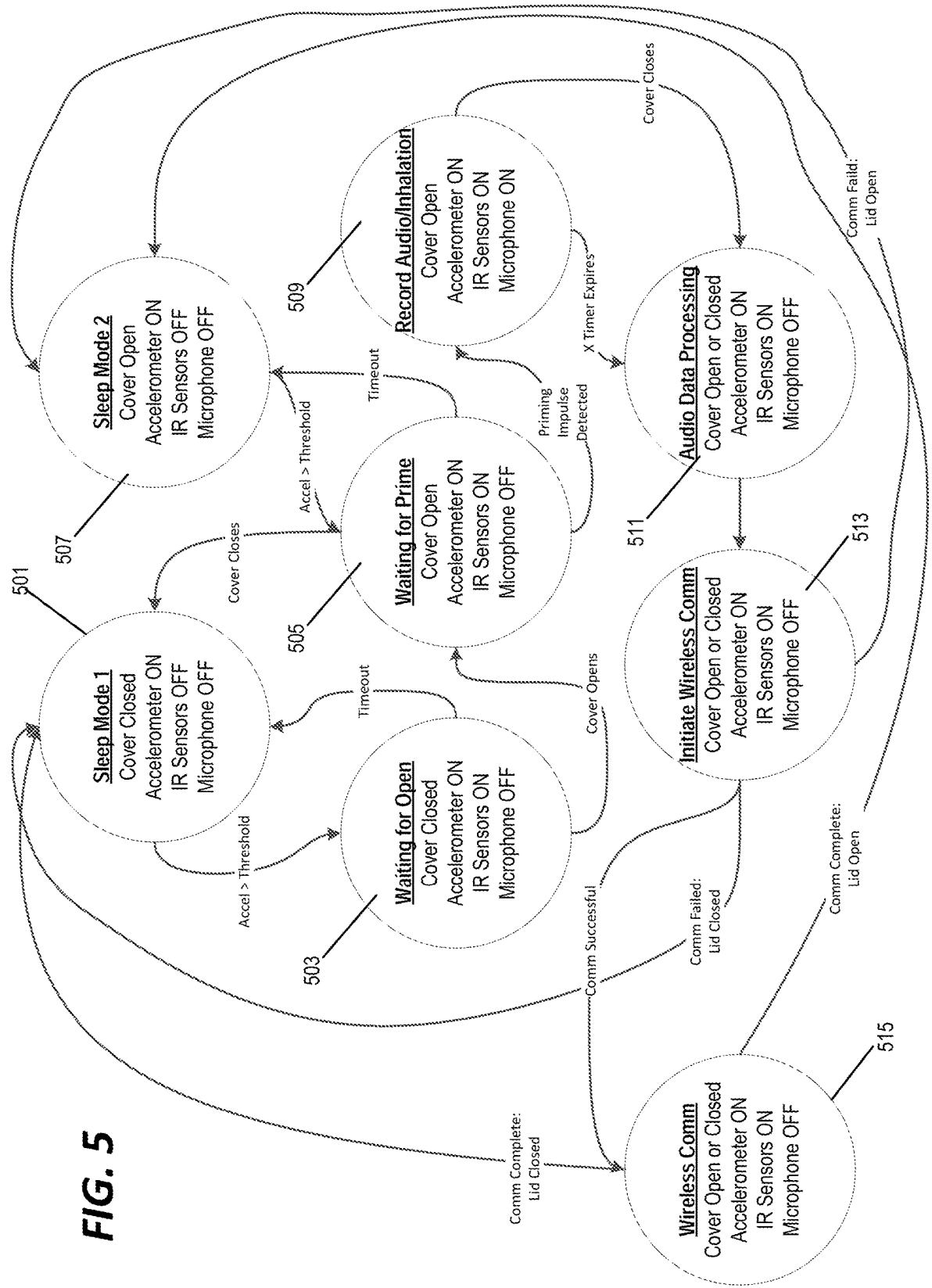
FIG. 5 is a state diagram illustrating various operating states of the attachment of FIG. 2.

To provide for more robust operation, the controller in some constructions is programmed to operate in a number of "states" rather than executing a linear series of operations as illustrated in FIG. 4. FIG. 5 illustrates one example of a state diagram for controlling the operation of the attachment device. The device begins in "Sleep Mode 1" (state 501) where the controller believes that the device cover is closed. The accelerometer is turned on, but the IR sensor module and the microphone are both disabled. When the acceleration exceeds a threshold, the system moves into a "waiting to open" state (state 503). In this state, the accelerometer and the IR sensor module are both turned on and the cover is closed. If the system times-out before movement of the cover is detected, it returns to "Sleep Mode 1" (state 501). However, if the IR sensor module indicates that the cover is opened, the system moves to a "waiting for prime" state (state 505). Again, a system timeout can send the device into a "Sleep Mode 2" (state 507) where the IR sensor module is disabled to conserve power. Also, if the IR sensors indicate that the cover is closed at this stage, the system returns to "Sleep Mode 1" (state 501). However, if the priming impulse is detected by the accelerometer, the system moves to a "Record Audio/Inhalation" state (state 509) in which the microphone is also powered on. Audio recording is terminated when either the cover is closed (as indicated by the IR sensors) or when a timer expires. In either case, the system moves to the "Audio Data Processing" state (state 511) where the microphone is powered off and the audio data is processed before being saved to memory.

After the data processing is complete, the system attempts to initiate wireless communication (entering the "Initiate Wireless Comm" state) (state 513). If communication fails, the system returns to either "Sleep Mode 1" (state 501) or "Sleep Mode 2" (state 503) depending on whether the IR sensor module indicates that the dispenser cover is open. However, if communication is successful, the system moves to a "Wireless Comm" state (state 515) where data is wirelessly transmitted to a terminal device such as a cell phone carried by the user. Once data has been successfully transmitted, it is deleted from the internal memory of the attachment device. After the wireless communication is complete, the system returns to either "Sleep Mode 1" (state 501) or "Sleep Mode 2" (state 507)—again, depending on whether the IR sensor module indicates that the dispenser cover is open.

Other constructions of the attachment may include additional sensors and functionality not illustrated or described above. Similarly, other constructions may include fewer sensors and few functional steps than those illustrated above. For example, in some constructions, steps 409 and 411 of FIG. 4 are omitted. In such constructions, the attachment does not monitor separately for a priming impulse and, instead, assumes that medicament is dispensed based on either (1) the opening of the mouthpiece (as detected by the IR sensor 305) or (2) the audible sound of the medicament being inhaled (as detected by the microphone 309).

Furthermore, in still other constructions, fewer sensors can be utilized. For example, in one construction, the IR sensor 307 is omitted, leaving only the accelerometer 305 and the microphone 309. As a result, steps 405 and 407 of FIG. 4 are omitted. The attachment monitors the accelerometer 305 to determine when the device is being handled and then activates the microphone 309. The microphone 309 is then monitors for the audible sound of the medicament being inhaled. Alternatively (or in addition), the output of the microphone 309 can be monitored to determine a sound associated with the priming action of the dry powder inhaler (i.e., the sound of the pill being crushed or of the priming lever 109 being moved). Once the relevant sound is detected, the attachment determines that the medicament has been dispensed and transmits relevant information to the cell phone (or other device).

In yet another construction, the microphone 309 is omitted and only the accelerometer 305 and the IR sensor 307 remain. In such embodiments, step 413 is omitted from the method of FIG. 4. The accelerometer 305 is used to detect handling of the device and to detect a priming impulse (i.e., movement of the priming lever 109). The IR sensor 307 is used to determine whether the mouthpiece of the inhaler is opened. Alternatively, the IR sensor 307 can be used to visually detect movement of the priming lever 109 (i.e., a dispensing of the medicament is detected when the priming lever 109 breaks the IR beam emitted by the IR sensor 307).

In still another construction, the microphone 309 and the IR sensor 307 are both omitted leaving only the accelerometer 305. In such embodiments, the accelerometer 305 is used to detect handling of the device (i.e., steps 401 & 403) and is also used to detect the priming impulse of the dispenser (steps 409 & 411). Steps 405,407, and 413 are omitted.

In another construction, the IR sensor is positioned to sense when the mouth of the patient is placed in proximity to the mouthpiece during medication use.

In some constructions, the attachment device 200 may include additional sensors to monitor galvanic skin response, oxygen saturation, and heart rate. These sensors can be passively activated, and their measurements obtained, by the fingers either in the normal course of handling and using the inhaler, or by activating specific buttons on the surface of the housing. Once these biometric parameters (for example, heart rate) are determined, the processor stores the data to the memory and attempts to initiate a wireless communication link to send the data to the patient's cell phone. Once the biometric data is sent, it is deleted from the local memory.

As described above, the wireless communication link is initiated whenever a usage event or heart rate event are concluded. The stored audio data and/or heart rate data is then uploaded to the computer server through a cell phone. However, in situations where a wireless link cannot be established, the data remains stored in the memory until the next wireless link is successfully established. Furthermore, in some constructions, the attachment device stores further information including, for example, a history of accelerometer readings that indicate movement of the dispenser device. In some constructions, this additional accelerometer data is also uploaded to the computer server whenever a wireless link is established (i.e., after a medication usage event or heart rate event).

Although not illustrated in the examples above, some constructions of the attachment device include a user interface. The user interface can include one or more indicators (e.g., LED, OLED, audible signals, visual signals, etc.) that indicate information regarding the operation of the attachment device (e.g., low battery, wireless comm established, etc.). The user interface can also include various buttons that, for example, establish pairing between the attachment device and a particular cell phone or perform a factory reset of the device. Lastly, in some constructions, the attachment device includes a vibration component that vibrates to call the attention of the user.

The vibration feature and other components of the user interface can be used in conjunction with an application running on the user's cell phone to help the user locate a lost dispenser. The user can initiate a signal from the cell phone that then causes the attachment device to vibrate, blink, or emit an audio signal.

Some constructions also utilize the user interface to notify the user when the attachment device is out of range and cannot establish a wireless link with the user's cell phone. If the attachment device is unable to connect with the cell phone, an indicator—such as, for example, a light, vibration, or tone—is initiated by the attachment device. Similarly, an application can be run on the user's cell phone that provides an indication on the cell phone when a link with the attachment device cannot be established. Therefore, the attachment device notifies the user when the attachment device is being taken out of range of the cell phone and the cell phone can be configured to notify the user when they are leaving the house without their medication dispenser.

In some constructions, the attachment device is further configured to determine whether the attachment device is coupled to a dispenser. For example, whenever the attachment device described above comes out of one of the "Sleep Modes," the IR sensor module will indicate whether a dispenser is "opened," "closed," or "not attached." In other constructions, the attachment device may include a mechanical switch or an ambient light sensor to detect whether the attachment device is properly coupled to a dispenser.

The array of sensors described above can also be monitored to establish a "use profile." In such constructions, the device will determine and store indications of whether the device was recently opened (based on the IR sensors), whether the device was recently primed/cocked (based on the accelerometer and microphone), whether a sound was recorded that could be an inhalation, and whether each of these events occurred within a temporal window that indicates a normal usage of the medication dispenser.

Figure 6A:
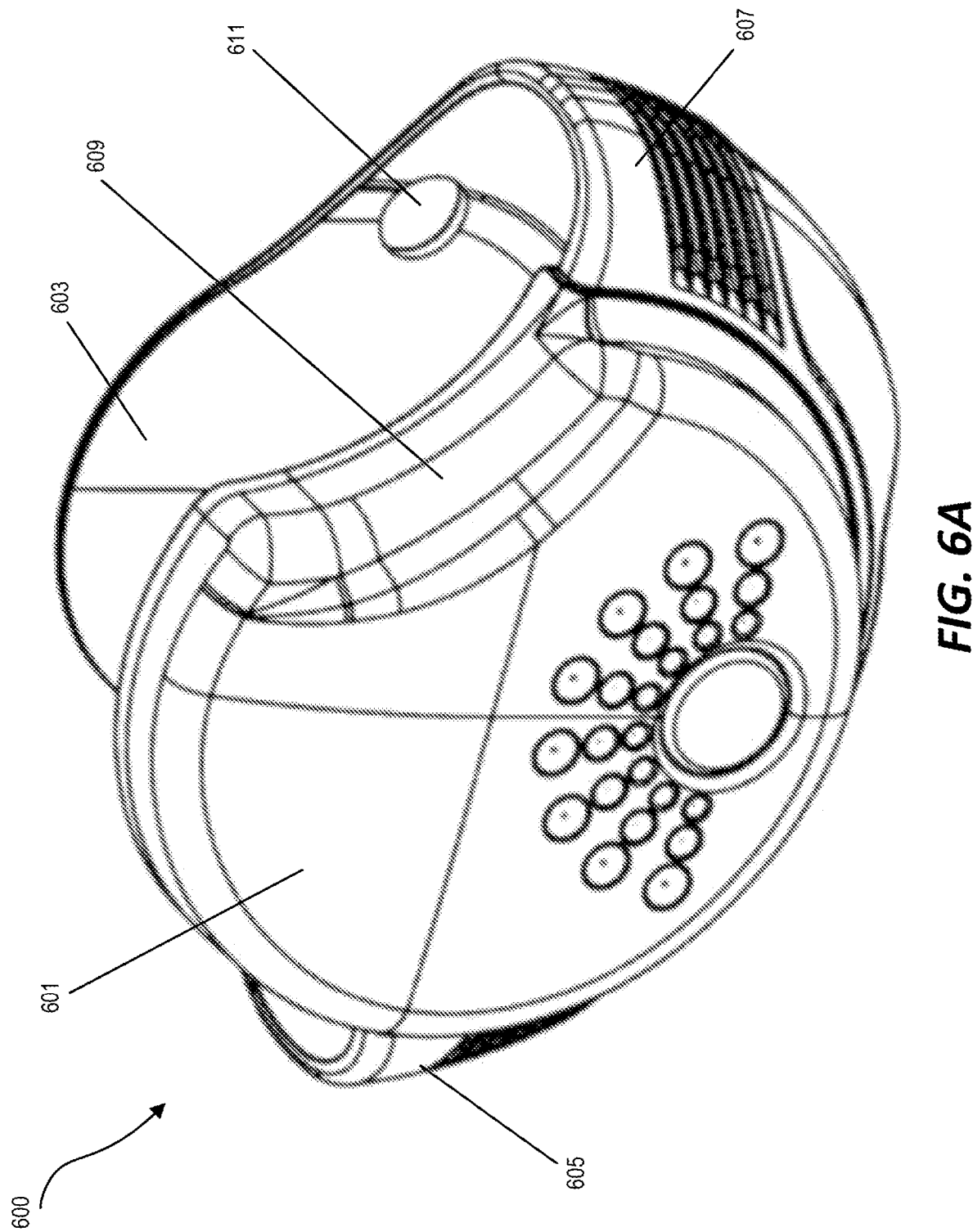
FIG. 6A is a perspective view of an attachment for use with a dry-powder inhaler.

FIG. 6A illustrates the exterior of another construction of an attachment 600 for use with a medicament dispensing device such as the Diskus dry-powder inhaler. The attachment again includes an upper body 601 and a lower body 603 connected by two side connection portions 605 and 607. The external casing of the upper body 601 is generally circular with a cut-out portion 609. The cut-out portion 609 provides greater access to the thumb grip 103 of the rotating dispenser body 101 (FIG. 1A) as well as visual access to the dose counter 105 when the dispenser is in the closed position. When the dispenser is in the opened position, the cut-out portion 609 provides greater access to the mouthpiece 111. The lower body 603 also includes a pair of screw holes 611 used to tighten pressure screws which are used to hold the attachment in place on the dispenser, as described in greater detail below. In some constructions, the upper body 601 or lower body 605 also includes a cut-out (not pictured) to ensure that a dose counter on the dispensing device is not covered by the attachment 600.

FIG. 6B provides a top view of the attachment 600. This view better illustrates the shape of the upper body 601 (including the cut-out portion 609). It also illustrates the shape of the side connection portions 605, 607 which join the upper body 601 to the lower body 603. As shown in FIG. 6B, the side connection portions 605, 607 are generally formed to conform to the shape of the medicament dispenser. The two side connection portions 605, 607 are separated by an opening 613 which can be used to push the dispenser out of the attachment 600 as necessary when the dispenser is being removed from the attachment 600.

Figure 6C:
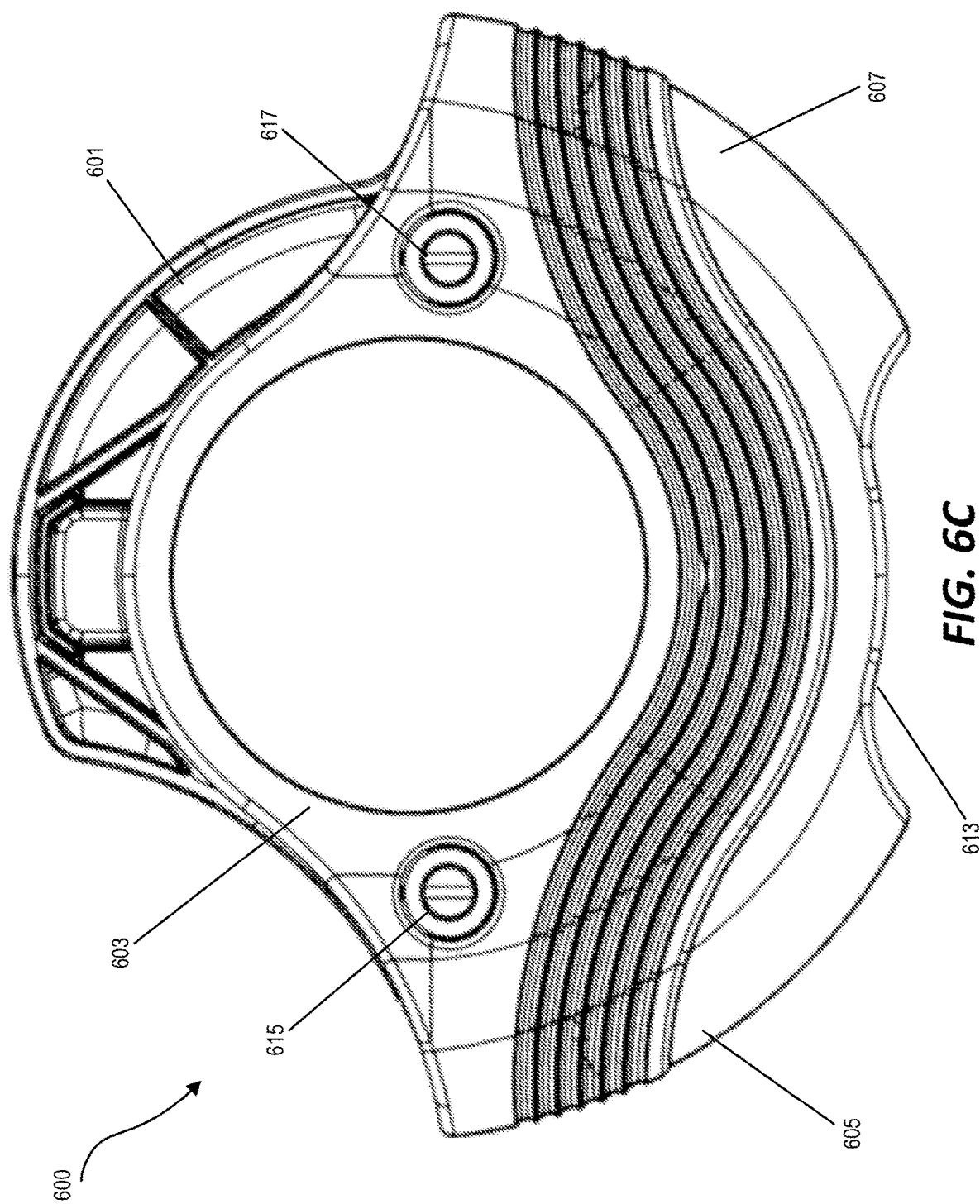
FIG. 6C is a bottom view of the attachment of FIG. 6A.

FIG. 6C shows the attachment 600 from the bottom. As shown in FIG. 6C, the upper body 601 extends beyond the lower body 603. Furthermore, from the bottom, the pair of friction screws 615, 617 can be seen. When the dispenser is inserted into the attachment, the friction screws 615, 617 are tightened into screw holes 611 to increase the friction between the dispenser and the upper body 601 of the attachment thereby securing the attachment 600 to the dispenser. Although this discussion refers to screws 615, 617 as "friction screws" that are used to secure the dispenser within the attachment, in other constructions, the size and material of the attachment 600 is configured to hold the dispenser device in place by a friction fit without the use of screws. In some such constructions, screws 615, 617 may be used to secure an external cover of the attachment 600 to the body of the attachment 600.

Figure 6E:
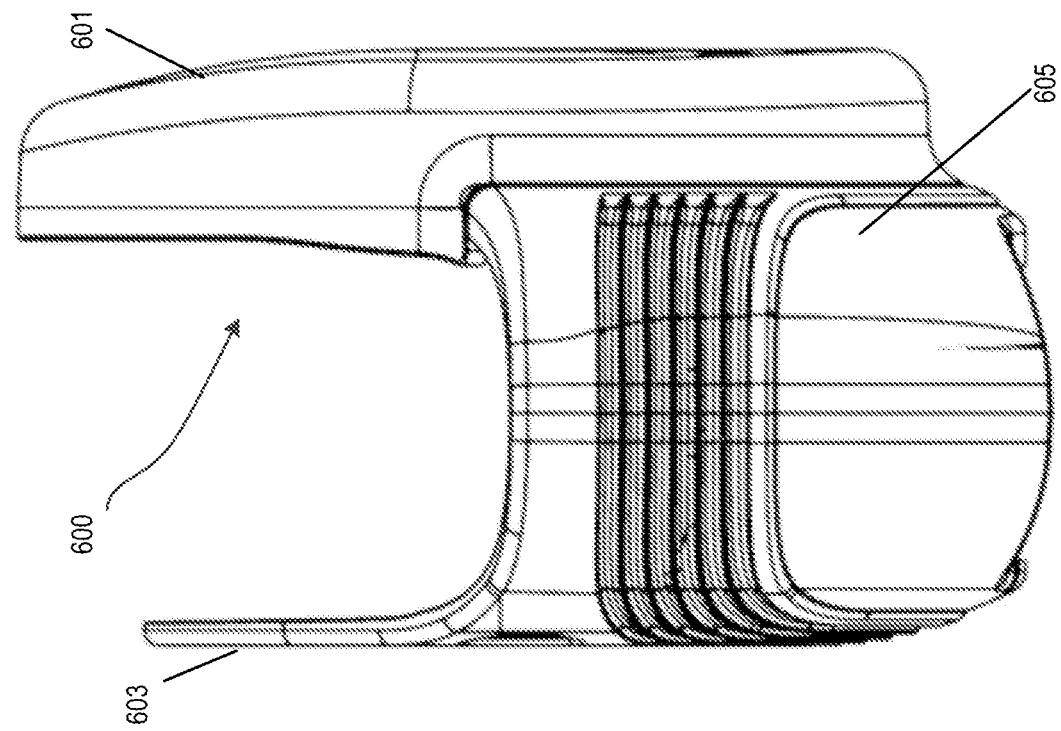
FIG. 6E is a left side view of the attachment of FIG. 6A.
Figure 6D:
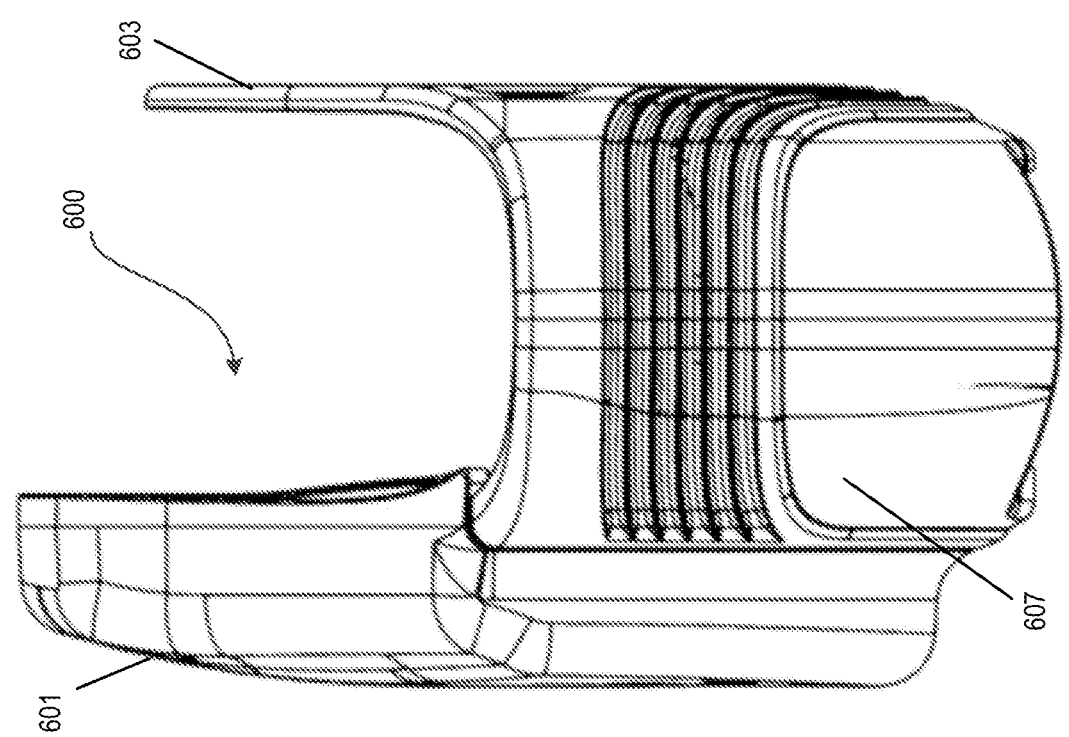
FIG. 6D is a right side view of the attachment of FIG. 6A.

FIGS. 6D and 6E show the attachment 600 from the left and the right sides. As shown in FIGS. 6D and 6E, the upper body 601 is thicker than the lower body 603. The upper body 601 is shaped to provide sufficient internal space to hold the processor 301, the wireless transceiver 311, the memory 303, and the various sensors employed to monitor the usage of the dispenser.

Figure 6F:
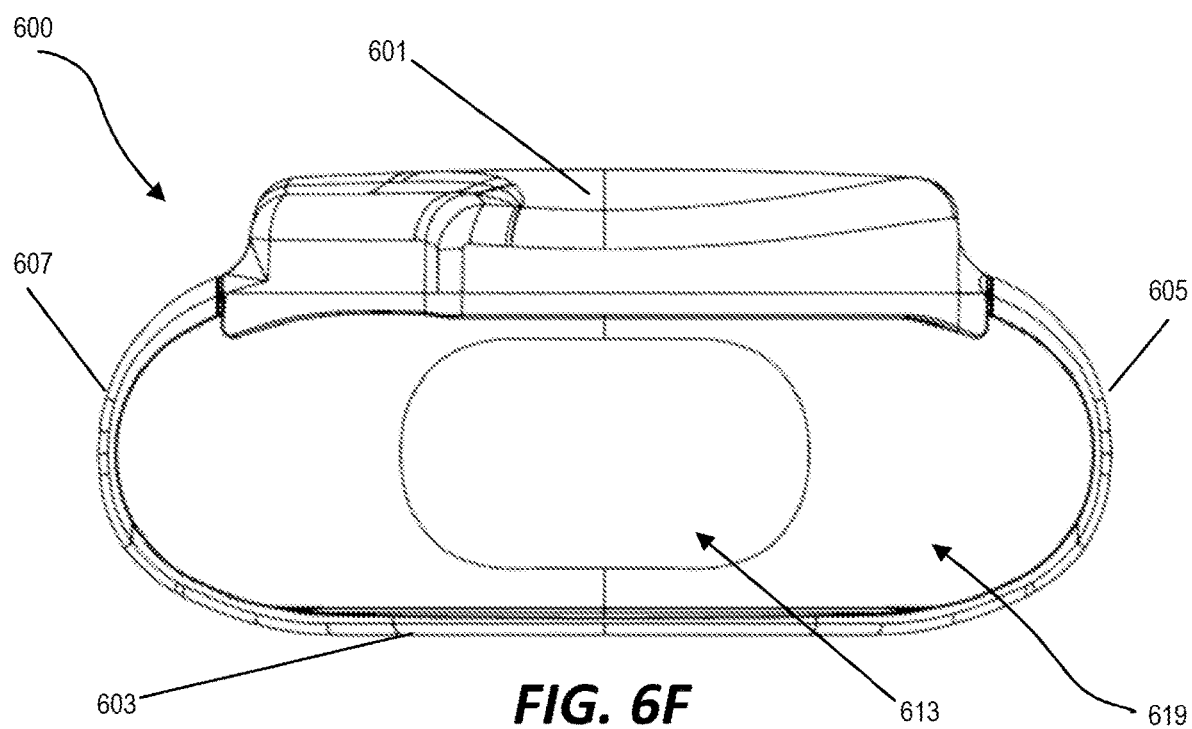
FIG. 6F is a front view of the attachment of FIG. 6A.

As shown in FIG. 6F, the arrangement of the upper body 601, the lower body 603, and the side connection portions 605, 607 forms a large opening 619 for receiving the dispenser. To couple the attachment 600 to the dispenser, the cover 107 of the dispenser is inserted into the larger opening 619 and the friction screws 615, 617 are tightened to hold the dispenser in place. As a result, the cover 107 is held stationary relative to the attachment 600 while the dispenser body 101 is allowed to rotate relative to the attachment 600.

Figure 6G:
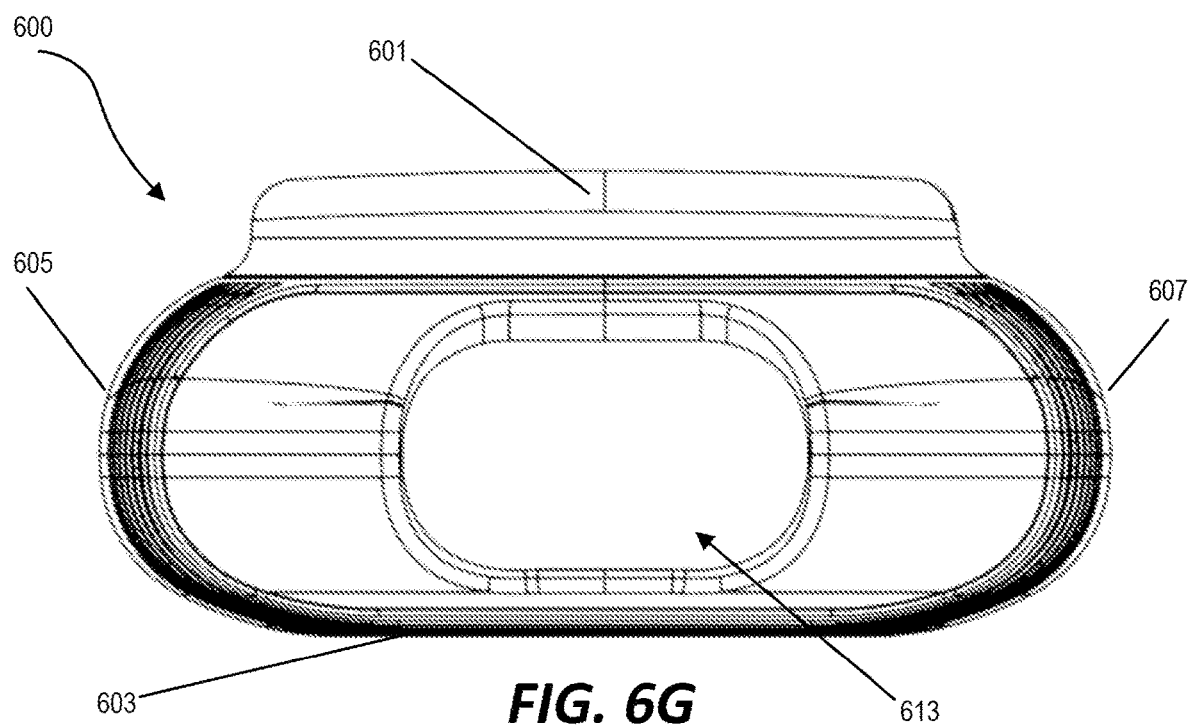
FIG. 6G is a rear view of the attachment of FIG. 6A.

As shown in FIG. 6G, the opening 613 is positioned opposite the larger opening 619. To decouple the attachment 600 from the dispenser, the friction screws 615, 617 are loosened and the user inserts one or more fingers into the opening 613 to push the dispenser through the larger opening 619 on the opposite side, thereby disengaging the dispenser from the attachment 600.

Although the examples illustrated above discuss an attachment that is adapted to be coupled to a Diskus-type dry powder inhaler, the sensing functionality and arrangements described above can be applied to other types of medicament dispensers. For example, an accelerometer can be incorporated into an attachment for use with a canister-style metered dose inhaler such as the cap housing described in U.S. Pub. No. 2009/0194104. Such an accelerometer can be used to detect dispensing of the medicament from the canister and then provide power to additional electronic components within the attachment.

Figure 7A:
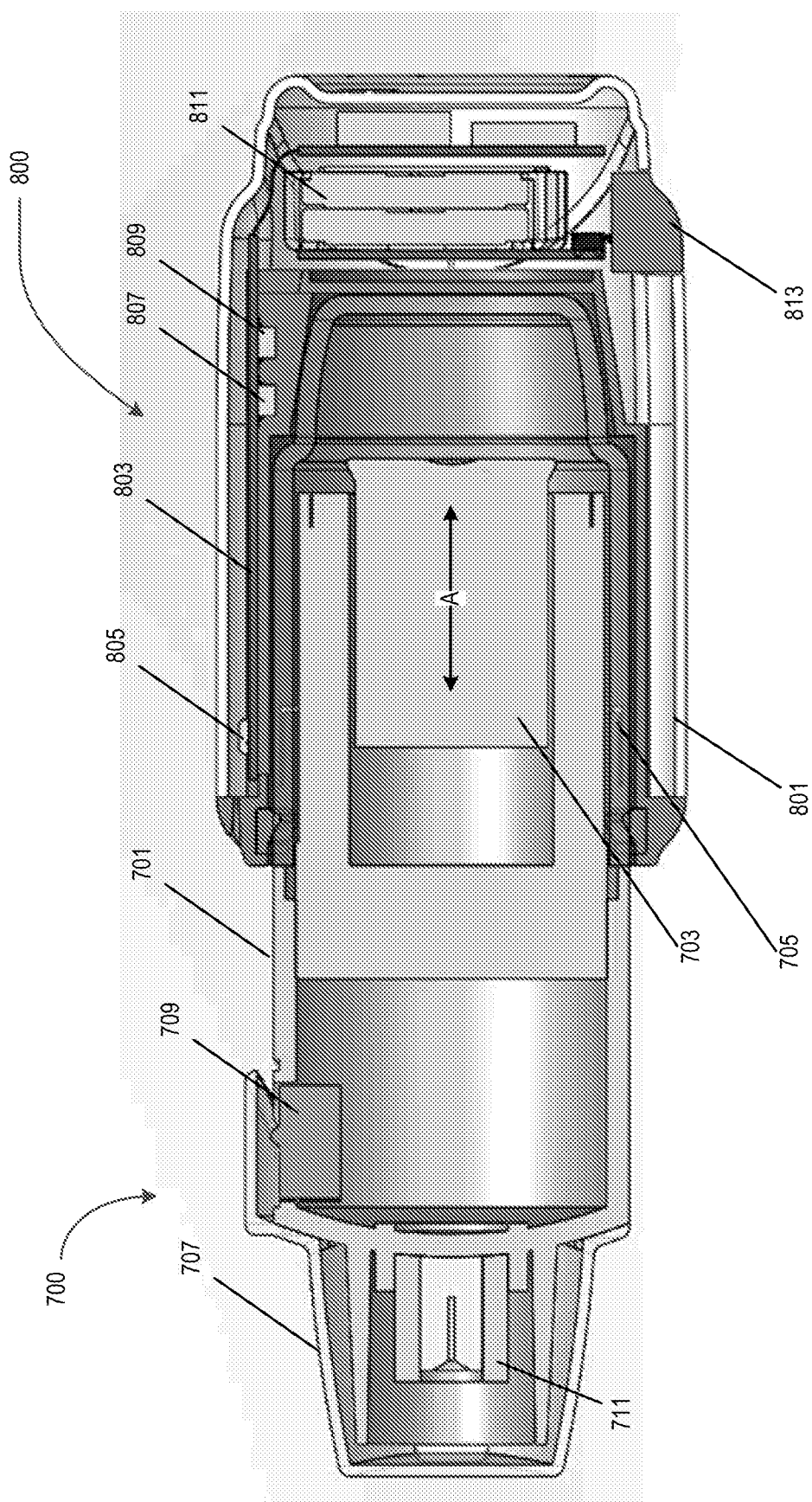
FIG. 7A is cross-sectional view of another construction of an attachment fitted to a soft mist inhaler (SMI).

FIG. 7A illustrates a construction of an attachment 800 configured for use with a medicament dispenser device such as the Respimat soft mist inhaler (SMI) 700 developed by Boehringer Inhelheim. The Respimat dispenser 700 includes a main body 701 with a cavity for receiving a medication canister 703. A cover 705 is then placed over the canister 703. Another cover 707 and a dispensing button 709 are positioned on the opposite end of the main body 701. The cover 707 is opened to reveal a mouthpiece 711 underneath.

To prime the Respimat dispenser 700 for use, the cover 705 is rotated relative to the main body 701. This causes the medicament canister 703 to move out of the cavity of the main body 701 along axis "A." When the cover 707 is opened and the button 709 is pressed, the medicament is dispensed through the mouthpiece 711 as the canister moves into the cavity of the main body 701 along axis "A."

The attachment 800 includes an external body 801 which is sized to fit around the exterior of the rotatable cover 705 of the Respimat dispenser device 700. A printed circuit board 803 is positioned within the external body 801 and, in this example, includes a microphone 805, an IR sensor 807, and an accelerometer 809. However, in other constructions, the attachment 800 may be fitted with additional sensors, alternative sensors, or fewer sensors. Similarly, the sensor may have different placement in other constructions. A pair of button-type batteries 811 is positioned at the distal end of the attachment and are electrically coupled to the circuit board 803. A button 813 is also positioned on the external body 801 of the attachment 800.

A described above in reference to FIGS. 4 and 5, the accelerometer 809 is used to bring the attachment out of a low-power "sleep mode" and to then apply electrical power from the batteries 811 to the microphone 805 and the IR sensor 807. Once out of the sleep mode, the IR sensor 807 monitors for the movement of the medicament canister 703 through the transparent cover 705 of the Respimat dispenser device 700. The attachment determines that the medicament has been dispensed when the canister 703 first moves to obstruct the IR sensor 807 and then moves again to a position that does not obstruct the IR sensor 807. Once dispensing is detected, the microphone 805 is activated to detect and measure sounds associated with the inhaled medicament. For example, the output of the microphone 805 can be used to measure inhalation characteristics of the patient using the medication and, together with application software running on the user's smartphone, provide feedback to a doctor or the patient.

Alternatively, in other constructions, the IR sensor 807 is omitted, leaving only the microphone 805 and the accelerometer 809. In such constructions, the accelerometer is used to detect handling of the attachment 800 and the Respimat dispenser device 700. Once handling is detected and power is applied to the microphone 805, the output of the microphone 805 is monitored for a "click" sound associated with the priming of the Respimat dispenser device 700 (i.e., the rotation of the transparent canister cover 705) Alternatively, the output of the microphone 805 can be monitored to detect when the button 709 of the dispenser device 700 is pressed indicating that medication has been dispensed.

In still other constructions, the positioning of the IR sensor 807 can be moved such that the IR sensor detects compression and decompression of a spring in the transparent base of the dispenser device 700 (which indicates priming and movement of the medication canister). This can be in addition to or instead of the IR sensor 807 positioned to directly detect canister movement from the side of the transparent base.

Figure 7B:
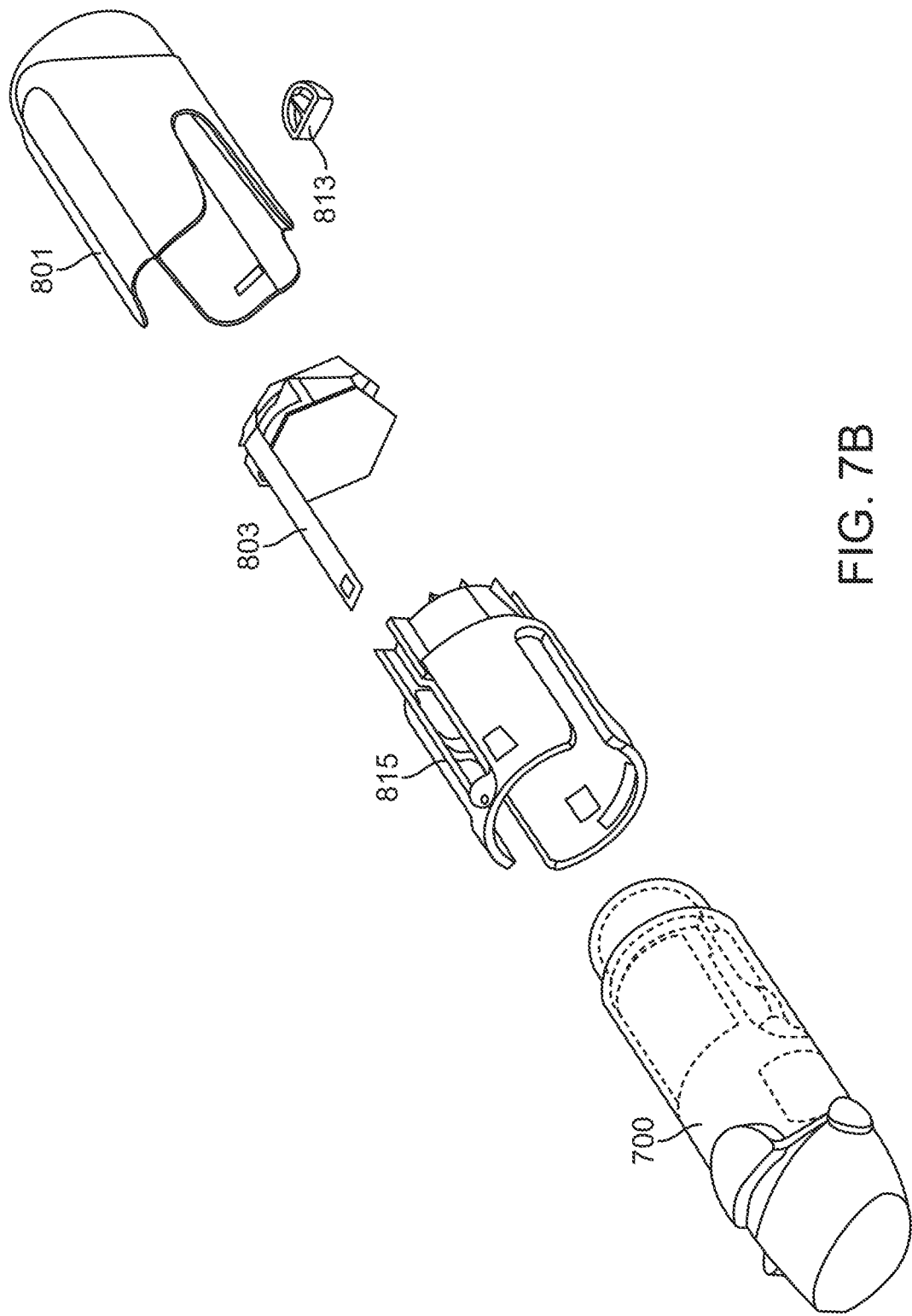
FIG. 7B is an exploded view of the attachment and soft mist inhaler (SMI) of FIG. 7A.

FIG. 7B shows an exploded view of the various components of the attachment 800. The Respimat dispenser device 700 fits into an internal receiving body 815 of the attachment 800. The internal receiving body 815 is sized and configured to be placed in close proximity with the external surfaces of the Respimat dispenser device 700 such that rotation of the attachment 800 (and, therefore, rotation of the internal receiving body 815) causes rotation of the transparent canister cover portion 705 of the Respimat dispenser device 700. A circuit board/logic portion 803 is formed to fit between the internal receiving body 815 of the dispenser and the external body 801. The attachment 800 may be configured to attach to the housing of the dispenser device 700 without requiring adhesive material or excessive force and can be done in a single one-step on/off procedure. The attachment housing design may include clear material so no labeling of the dispensing device 700 is covered. When attached, the attachment 800 does not interfere with or restrict use of the dispensing device 700.

Figure 8A:
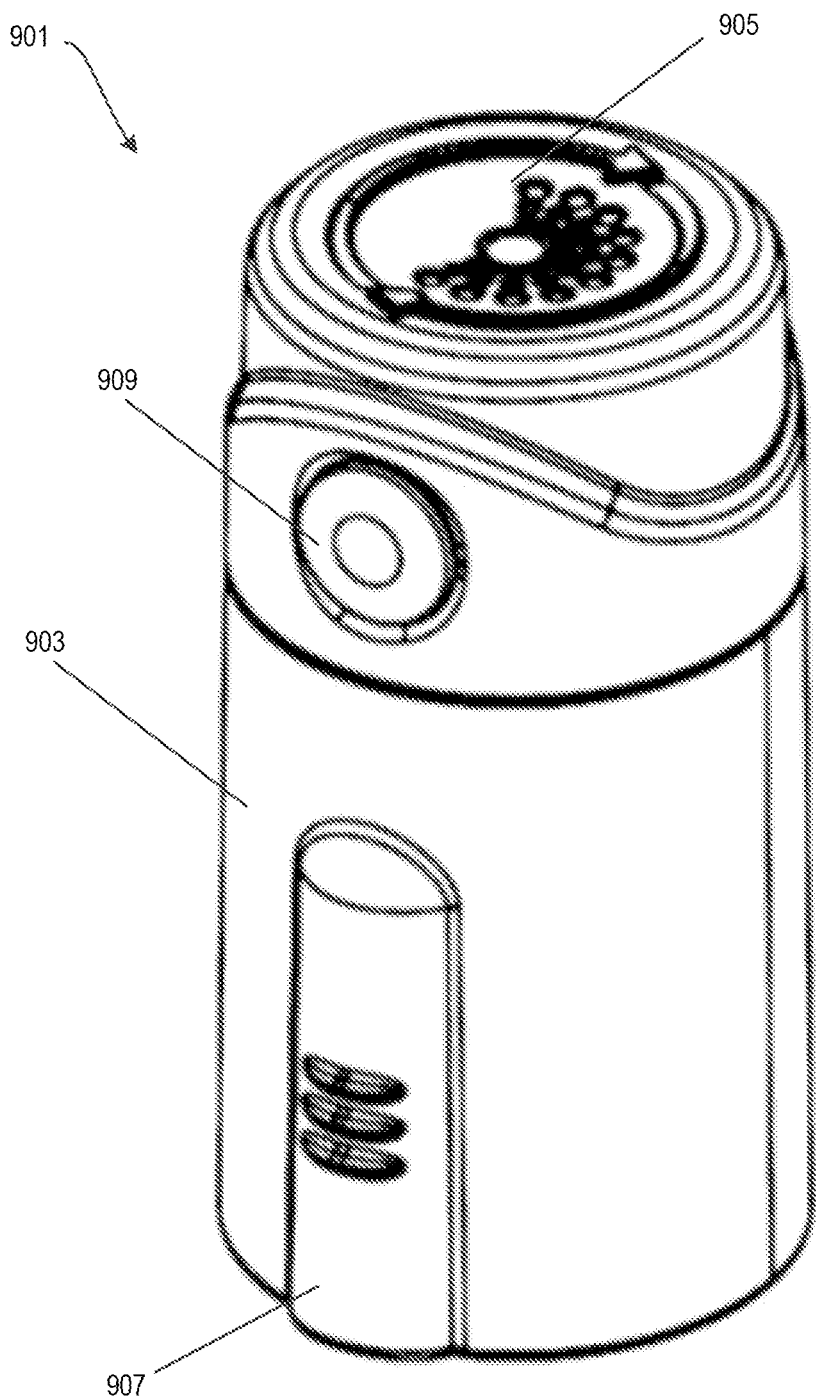
FIG. 8A is a perspective view of another attachment for a soft mist inhaler (SMI).
Figure 8C:
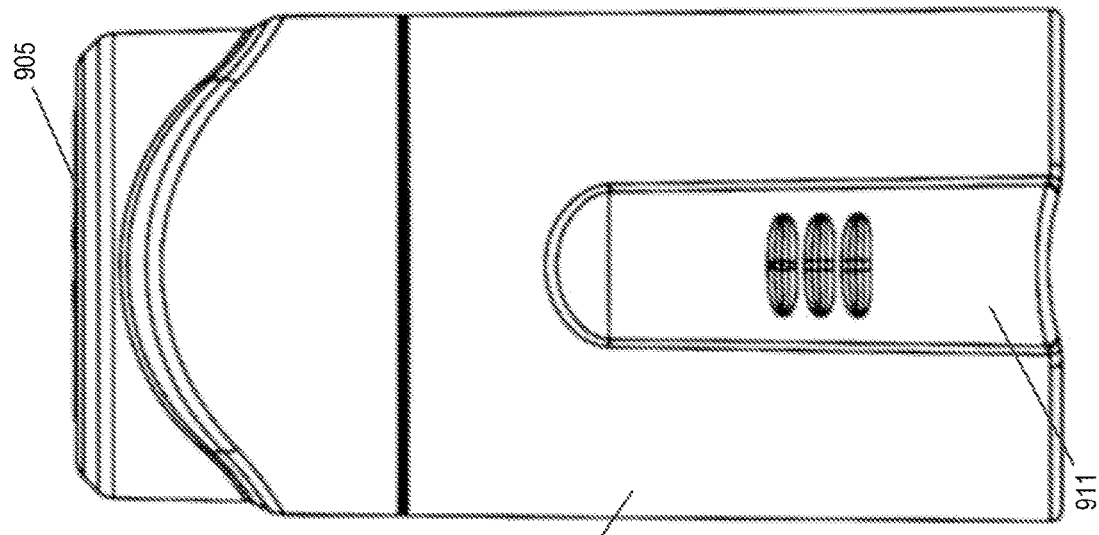
FIG. 8C is a rear view of the attachment of FIG. 8A.
Figure 8B:
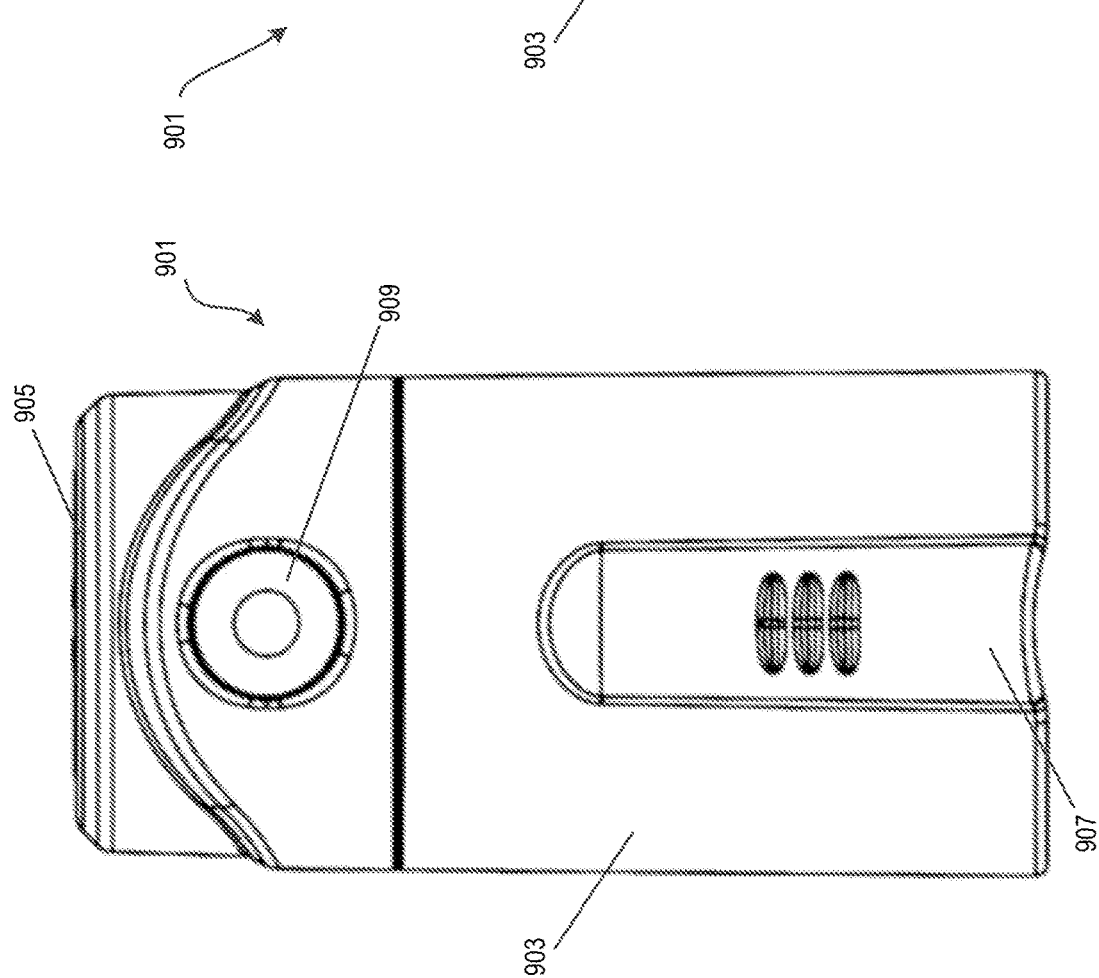
FIG. 8B is a front view of the attachment of FIG. 8A.
Figure 8F:
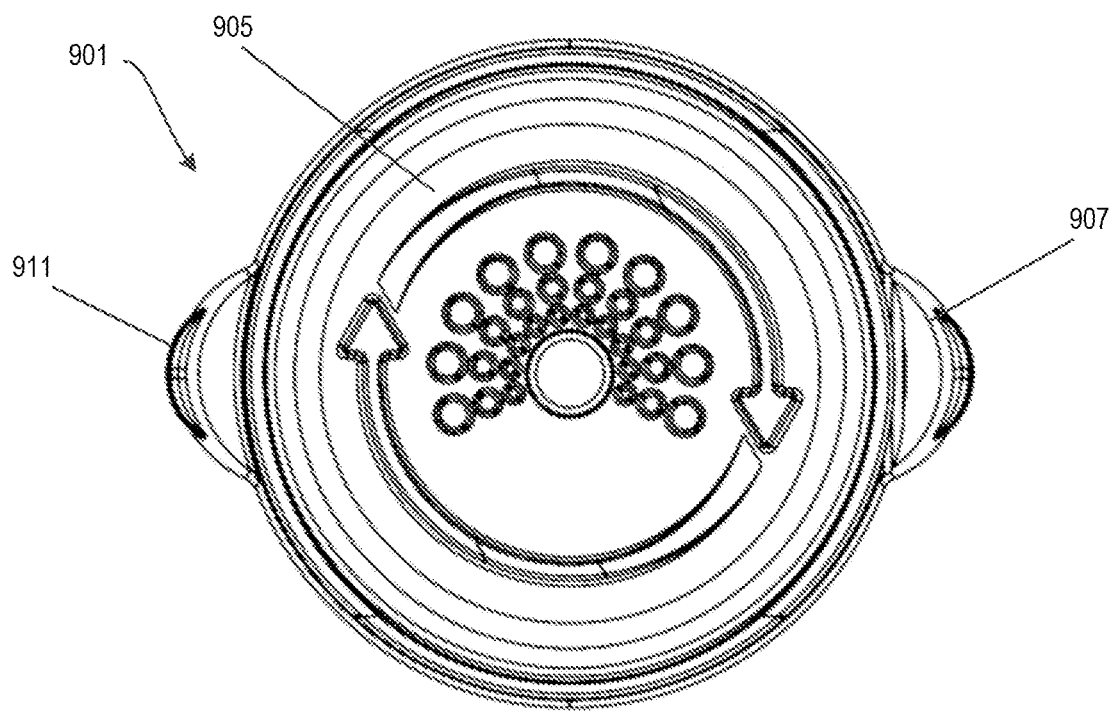
FIG. 8F is a top view of the attachment of FIG. 8A.
Figure 8G:
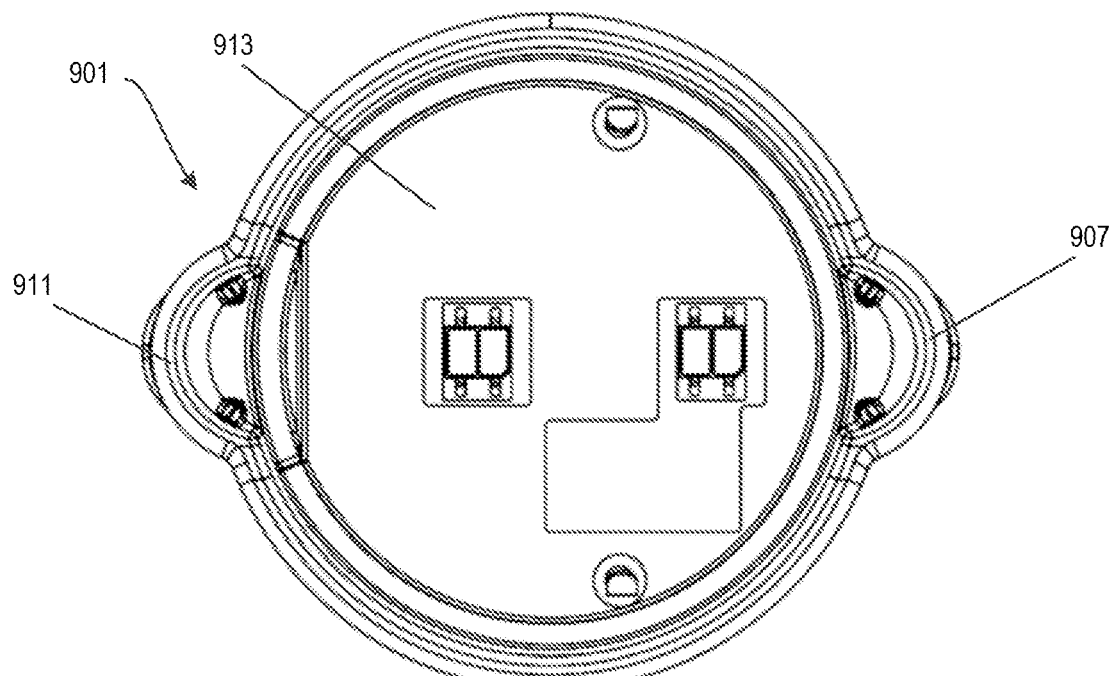
FIG. 8G is a bottom view of the attachment of FIG. 8A.

FIGS. 8A-8G illustrate another example of an attachment device 901 for use with a Respimat-type medicament dispenser. As shown in FIG. 8A, the external surface of the attachment device 901 includes a substantially cylindrical sheath body 903 and a top surface 905. As show in FIGS. 8B and 8C, the cylindrical sheath body 903 includes a slight beveled portion near the top surface 905 such that the diameter of the top surface 905 is slightly smaller than the diameter of an opening at the opposite end of the sheath body 903. The sheath body 903 is also formed to include a protrusion 907 formed to receive a similarly shaped protrusion of the transparent cover 705 of the Respimat dispenser device 700. Another similarly sized protrusion 911 is formed on the opposite side of the sheath body 903 (see, FIGS. 8C, 8D, and 8E). A button 909 is positioned on the sheath body 903 near the top surface 905.

Thus, the invention provides, among other things, an attachment device for monitoring the usage of a medication dispenser. The attachment device come out of a low-powered "sleep mode" when it detects that the dispenser is being handled and then provides power to additional components that consume more power. The attachment device can be configured to fit with a variety of different dispenser devices including, for example, a canister-type metered dose inhaler, a Diskus-type dry powder inhaler, and a Respimat soft mist inhaler. Various features and advantages of the invention are set forth in the following claims.

What is claimed is:

1. A method of monitoring usage of a medicament dispenser with a monitoring attachment, the method comprising:
    detecting, with an infrared sensor of the monitoring attachment, a first signal indicative of preparing to dispense medicament by the medicament dispenser, the first signal detected in response to movement of a body of the medicament dispenser relative to a cover in a first direction;
    in response to detecting the first signal, applying power to a microphone of the monitoring attachment;
    recording audio captured by the microphone; and
    transmitting a signal comprising the captured audio to a monitoring device for monitoring usage of the medicament dispenser.

2. The method of claim 1, wherein the infrared sensor is positioned to detect movement of a feature on the body, the feature selected from a group consisting of: a ridge for air intake and a dose counter window, wherein the movement of the feature corresponds to movement of the body relative to the cover.

3. The method of claim 1, wherein the movement of the body relative to the cover in the first direction reveals a mouthpiece of the medicament dispenser through which medicament may be dispensed.

4. The method of claim 3, further comprising:
    detecting, with the infrared sensor, a second signal indicative of closing of the cover, the second signal detected in response to movement of the body relative to the cover in a second direction opposite the first direction which occludes the mouthpiece; and
    in response to detecting the second signal, ceasing to apply power to the microphone.

5. The method of claim 1, wherein the movement of the body relative to the cover in the first direction corresponds to priming of the medicament dispenser which, when primed, can dispense medicament.

6. The method of claim 1, wherein the movement of the body relative to the cover comprises a rotation of the body relative to the cover.

7. The method of claim 1, wherein recording the audio captured by the microphone comprises:
   recording a sound of inhalation of medicament dispensed by the medicament dispenser.

8. The method of claim 7, wherein recording the audio further comprises:
   recording a sound of priming of the medicament dispenser from movement of a priming lever of the medicament dispenser.

9. The method of claim 1, wherein the monitoring attachment is coupled to the cover and does not affect the movement of the body relative to the cover.

10. The method of claim 1, further comprising determining a time and a date of the dispensing of the medicament, and wherein the signal further comprises the time and the date of the dispensing.

11. A monitoring attachment attachable to a medicament dispenser for monitoring usage of a medicament dispenser, comprising:
   a housing comprising an exterior surface attachable to a cover of the medicament dispenser, wherein the monitoring attachment does not affect operation of the medicament dispenser;
   an infrared sensor configured to detect a first signal indicative of preparing to dispense medicament by the medicament dispenser, the first signal detected in response to movement of a body of the medicament dispenser relative to a cover in a first direction;
   a microphone configured to capture audio;
   a power control circuit configured to apply power to the microphone in response to detecting the first signal; and
   a wireless transmitter configured to transmit a signal comprising the captured audio to a monitoring device for monitoring usage of the medicament dispenser.

12. The monitoring attachment of claim 11, wherein the infrared sensor is positioned to detect movement of a feature on the body, the feature selected from a group consisting of: a ridge for air intake and a dose counter window, wherein the movement of the feature corresponds to movement of the body relative to the cover.

13. The monitoring attachment of claim 11, wherein the movement of the body relative to the cover in the first direction reveals a mouthpiece of the medicament dispenser through which medicament may be dispensed.

14. The monitoring attachment of claim 13,
   wherein the infrared sensor is further configured to detect a second signal indicative of closing of the cover, the second signal detected in response to movement of the body relative to the cover in a second direction opposite the first direction which occludes the mouthpiece; and
   wherein the power control circuit is configured to cease power to the microphone in response to detecting the second signal.

15. The monitoring attachment of claim 11, wherein the movement of the body relative to the cover in the first direction corresponds to priming of the medicament dispenser which, when primed, can dispense medicament.

16. The monitoring attachment of claim 11, wherein the movement of the body relative to the cover comprises a rotation of the body relative to the cover.

17. The monitoring attachment of claim 11, wherein the audio captured comprises a sound of inhalation of medicament dispensed by the medicament dispenser.

18. The monitoring attachment of claim 17, wherein the audio captured further comprises a sound of priming of the medicament dispenser from movement of a priming lever of the medicament dispenser.

19. The monitoring attachment of claim 11, wherein the monitoring attachment is coupled to the cover and does not affect the movement of the body relative to the cover.

20. The monitoring attachment of claim 11, wherein the wireless transmitter is further configured to transmit a time and a date of the dispensing of the medicament with the signal.

* * * * *